US011957399B2

(12) United States Patent
Canady et al.

(10) Patent No.: US 11,957,399 B2
(45) Date of Patent: *Apr. 16, 2024

(54) SYSTEM AND METHOD FOR COMBINATION OF COLD ATMOSPHERIC PLASMA TREATMENT WITH RADIATION AND CHEMOTHERAPY

(71) Applicant: Jerome Canady Research Institute for Advanced Biological and Technological Sciences, Takoma Park, MD (US)

(72) Inventors: Jerome Canady, Lakeland, FL (US); Taisen Zhuang, Vienna, VA (US); Xiaoqian Cheng, Fairfax, VA (US)

(73) Assignee: JEROME CANADY RESEARCH INSTITUTE FOR ADVANCED BIOLOGICAL AND TECHNOLOGICAL SCIENCES, Takoma Park, MD (US)

( * ) Notice: Subject to any disclaimer, the term of this patent is extended or adjusted under 35 U.S.C. 154(b) by 897 days.

This patent is subject to a terminal disclaimer.

(21) Appl. No.: 16/933,782

(22) Filed: Jul. 20, 2020

(65) Prior Publication Data

US 2021/0015537 A1 Jan. 21, 2021

Related U.S. Application Data

(60) Provisional application No. 62/876,355, filed on Jul. 19, 2019.

(51) Int. Cl.
*A61B 18/04* (2006.01)
*A61B 34/00* (2016.01)
*A61B 18/00* (2006.01)

(52) U.S. Cl.
CPC ............ *A61B 18/042* (2013.01); *A61B 34/25* (2016.02); *A61B 2018/00494* (2013.01); *A61B 2034/256* (2016.02)

(58) Field of Classification Search
CPC .......... A61B 2018/00583; A61B 34/25; A61B 18/042; A61B 2018/00494;
(Continued)

(56) References Cited

U.S. PATENT DOCUMENTS 9,521,736 B2 * 12/2016 Jacofsky .................. A61N 1/44
9,999,462 B2    6/2018 Canady et al.
(Continued)

FOREIGN PATENT DOCUMENTS

WO    2016079742 A1    5/2016
WO    2018191265 A1    10/2018

OTHER PUBLICATIONS

Siegel R, Naishadham D, Jemal A. Cancer statistics, 2012. CA Cancer J Clin. 2012; 62:10-29.
(Continued)

*Primary Examiner* — Jason E Flick
(74) *Attorney, Agent, or Firm* — 24IP Law Group USA, PLLC; Timothy R DeWitt

(57) ABSTRACT

A method for applying cold atmospheric plasma treatment to target tissue comprising the steps of selecting through a graphical user interface a particular soft tissue sarcoma cell line associated with target tissue, retrieving, with said computing device, settings data associated with said selected soft tissue sarcoma cell line from a database of cell line data and associated settings data in a storage, and applying, with said computing device, said retrieved settings data to a cold atmospheric plasma system.

4 Claims, 21 Drawing Sheets

(58) Field of Classification Search
CPC ........ A61B 2034/256; A61M 2205/05; A61M 35/30; A61M 2202/0208
See application file for complete search history.

(56) References Cited

U.S. PATENT DOCUMENTS

| | | | |
|---|---|---|---|
| 10,213,614 B2 | 2/2019 | Keidar et al. | |
| 10,405,913 B2 | 9/2019 | Canday et al. | |
| 2014/0171854 A1* | 6/2014 | Jacofsky | A61B 18/042 604/23 |
| 2014/0378897 A1 | 12/2014 | Keidar et al. | |

OTHER PUBLICATIONS

Chu DZ, Lang NP, Thompson C, Osteen PK, Westbrook KC. Peritoneal Carcinomatosis in non-gynecologic malignancy. Cancer. 1989;63:364-7.

Sadeghi B, Arvieux C, Glehen O, et al. Peritoneal carcinomatosis from non-gynecologic Smalignancies. Results from the EVOCAPE 1 multicentric prospective study. Cancer.2000;88:358-63.

Glehen O, Osinky D, Cotte E, Kwiatkowski F, Freyer G, Issac S, Trillet-Ienoir V, Sayagbeaujard AC, Francois Y, Vignal J, et al. Intraperitoneal chemohyperthermia using a closed abdominal procedure and cytoreductive surgery for the treatment of peritoneal carcinomatosis: morbidity and mortality analysis of 216 onsecutive procedures. Ann Surg Oncol. 2003;10(8):863-9.

Glockzin G, Rochon J, Arnold D, Sa L, Klebl F, Zeman F, Koller M, Schlitt HJ, Piso P. A prospective multicenter phase II study evaluating multimodality treatment of patients with peritoneal carcinomatosis arising from appendiceal and colorectal cancer: the combatac trial. BMC Cancer. 2013; 13:67.

Jayne DG, Fook S, Loi C, Seow-Choen F. Peritoneal carcinomatosis from colorectal cancer. Br J Surg. 2002; 89:1545-50.

Piso P, Arnold D. Multimodal treatment approaches for peritoneal carcinosis in colorectal cancer. Dtsch Arztebl Int. 2011; 108(47):802-8.

Kulu Y, Muller-stich B, Buchler MW, Ulrich A. Surgical treatment of peritoneal carcinomatosis: current treatment modalities. Langenbeck's Arch Surg. 2013;399(1):41-53.

Franko J, Shi Q, Goldman CD, et al. Treatment of Colorectal peritoneal carcinomatosis with systemic chemotherapy: a pooled analysis of north central cancer treatment group phase III trials n9741 and n9841. J Clin Oncol. 2012; 30:263-7.

Verwaal VJ, van Ruth S, de Bree E et al. Randomized trial of cytoreduction and hyperthermic intraperitoneal chemotherapy versus systemic chemotherapy and palliative surgery in patients with peritoneal carcinomatosis of colorectal cancer. J Clin Oncol. 2003; 21:3737-43.

Riss S, Mohamed F, Dayal S, Cecil T, Stift A, Bachleitner-Hofmann T, Moran B. Peritoneal Metasases from colorectal cancer: patient selection for cytoreductive surgery and Hyperthermic Intraperitoneal chemotherapy. Eur J Surg Oncol. 2013; 39 (9):931-7.

Elias D, Gilly F, Quenet F, et al. Peritoneal colorectal carcinomatosis treated with surgery and Perioperative Intraperitoneal Chemotherapy: Retrospective analysis of 523 patients from a multicentric French study. J Clin Oncol. 2010; 28:63-8.

K.H. Becker, K.H. Shoenbach and J.G. Eden "Microplasma and applications" J. Phys. D.: Appl. Phys. 39, R55-R70 (2006).

E. Stoffels, I.E Kieft, R.E.J Sladek, L.J.M van den Bedem, E.P van der Laan, M. Steinbuch "Plasma needle for in vivo medical treatment: recent developments and perspectives" Plasma Sources Sci. Technol. 15, S169-S180 (2006).

Laroussi M, Kong M, Morfill G, Stolz W, editors. Plasma medicine. Cambridge; 2012.

Morfill GE, Kong MG, Zimmermann JL. Focus on plasma medicine. Review. New J Phys. 2009; 11:115011.

Keidar M. Plasma for cancer treatment. Plasma Source Sci Technol. 2015;24:033001.

Fridman G, Friedman G, Gutsol A, Shekhter AB, Vasilets VN, Fridman A. Applied plasma medicine. Plasma Process Polym. 2008;5:503.

Vandamme M, Robert E, Pesnel S, Barbosa E, Dozias S, Sobilo J, Lerondel S, Le Pape A, Pouvesle JM. Antitumor effect of plasma treatment on U87 Glioma Xenografts: preliminary results. Plasma Process Polym. 2010;7:264.

Keidar M, Walk R, Shashurin A, Srinivasan P, Sandler A, Dasgupta S, Ravi R, Guerrero-Preston R, Trink B. Cold plasma selectivity and the possibility of a paradigm shift in cancer therapy. Br J Cancer. 2011;105:1295.

Vandamme M, Robert E, Lerondel S, Sarron V, Ries D, Dozias S, Sobilo J, Gosset D, Kieda C, Legrain B, Pouvesle J-M, Le Pape A. ROS implication in a new antitumor strategy based on non-thermal plasma. Int J Cancer. 2011;130:2185.

Metelmann HR. What kind of impact is possible by plasma-jet in head and neck cancer?, The 2nd International Workshop on Plasma for Cancer Treatment, Nagoya, Japan, Mar. 2015.

Canady J. "Development and clinical application of hybrid and cold atmospheric plasma combined with systemic chemotherapy and selective 3D conformal radiation therapy: A novel approach to the treatment of peritoneal metastases from colorectal cancer." The 2nd International Workshop on Plasma for Cancer Treatment, Nagoya, Japan, Mar. 2015.

Metelmann HR, Nedrelow DS, Seebauer C, Schuster M, von Woedtke T, Weltmann K-D, Kindler S, Metelmann PH, Finkelstein SE, Von Hoff DD, Podmelle F. Head and neck cancer treatment and physical plasma. Clin Plasma Med. 2015;3:17-23.

Yan D, Sherman J H and Keidar M, "Cold atmospheric plasma, a novel promising anti-cancer treatment modality," Oncotarget. 8 15977-15995 (2017).

Keidar M, Beilis II. Plasma Engineering: application in aerospace, nanotechnology and bionanotechnology. Oxford: Elsevier; 2013.

Hirst A M, Frame F M, Arya M, Maitland N J and O'Connell D, "Low temperature plasmas as emerging cancer therapeutics: the state of play and thoughts for the future," Tumor Biol. 37 7021-7031 (2016).

Vandamme M, Robert E, Dozias S, Sobilo J, Lerondel S, Le Pape A and Pouvesle J-M, "Response of human glioma U87 xenografted on mice to non thermal plasma treatment," Plasma Med. 1 27-43 (2011).

Brulle L, Vandamme M, Ries D, Martel E, Robert E, Lerondel S, Trichet V, Richard S, Pouvesle J M and Le Pape A, "Effects of a Non thermal plasma treatment alone or in combination with gemcitabine in a MIA PaCa2-luc orthotopic pancreatic carcinoma model," PLoS One. 7 e52653 (2012).

Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," Plasma Process. Polym. 12 1400-1409 (2015).

Ahn H J, Kim K II, Kim G, Moon E, Yang S S and Lee J S, "Atmospheric-pressure plasma jet induces apoptosis involving mitochondria via generation of free radicals,". PLoS One. 6 e28154 (2011).

Ja Kim S, Min Joh H and Chung T H, "Production of intracellular reactive oxygen species and change of cell viability induced by atmospheric pressure plasma in normal and cancer cells," Appl. Phys. Lett. 103 153705 (2013).

Yan D, Talbot A, Nourmohammadi N, Sherman J H, Cheng X and Keidar M, "Toward understanding the selective anticancer capacity of cold atmospheric plasma—a model based on aquaporins (Review)," Biointerphases. 10 040801 (2015).

Yan D, Xiao H, Zhu W, Nourmohammadi N, Zhang L G, Bian K and Keidar M, "The role of aquaporins in the anti-glioblastoma capacity of the cold plasma-stimulated medium," J. Phys. D. Appl. Phys. 50 055401 (2017).

Yan D, Talbot A, Nourmohammadi N, Cheng X, Canady J, Sherman J and Keidar M, "Principles of using cold atmospheric plasma stimulated media for cancer treatment," Sci. Rep. 5 18339 (2015).

Ma Y, Ha C S, Hwang S W, Lee H J, Kim G C, Lee K W and Song K, "Non-thermal atmospheric pressure plasma preferentially induces

(56) References Cited

OTHER PUBLICATIONS apoptosis in p53-mutated cancer cells by activating ROS stress-response pathways," PLoS One. 9 e91947 (2014).

Sablina A A, Budanov A V, Ilyinskaya G V, Larissa S, Kravchenko J E and Chumakov P M, "The antioxidant function of the p53 tumor suppressor," Nat. Med. 11 1306 (2005).

Maillet A and Pervaiz S, "Redox regulation of p53, redox effectors regulated by p53: a subtle balance," Antioxid. Redox Signal. 16 1285-1294 (2012).

Naciri M, Dowling D and Al-Rubeai M, "Differential sensitivity of mammalian cell lines to non-thermal atmospheric plasma," Plasma Process. Polym. 11 391-400 (2014).

Fearon E F and Vogelstein B, "A genetic model for colorectal tumorigenesis," Cell. 61 759-767 (1990).

Yan D, Cui H, Zhu W, Nourmohammadi N, Milberg J, Zhang L G, Sherman J H and Keidar M, "The specific vulnerabilities of cancer cells to the cold atmospheric plasma-stimulated solutions," Sci. Rep. 7 4479 (2017).

Friedman A, Friedman G. Plasma medicine. Hoboken: Wiley; 2013.

\* cited by examiner

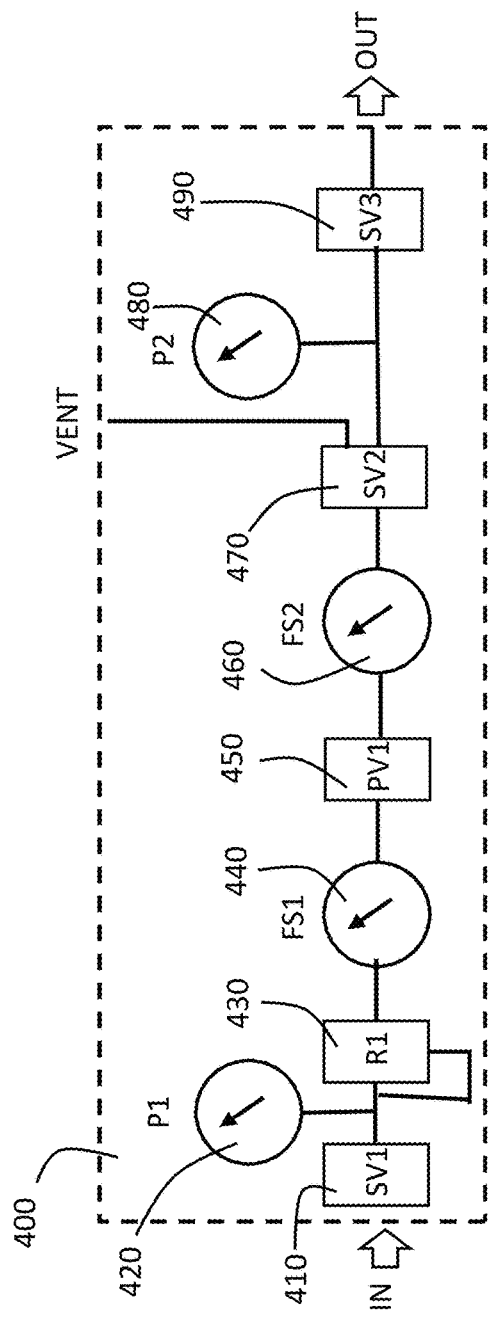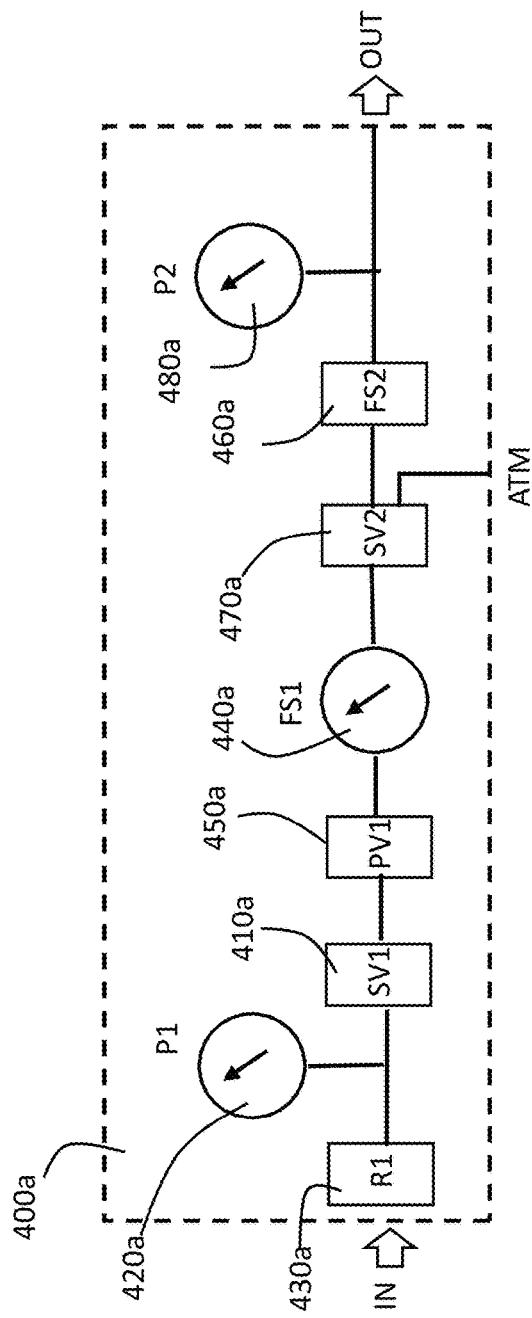

Recommended Treatment Conditions for Canady Helios Cold Plasma on Cancers

| Tissue | Cancer type | Flow Rate (LPM) | Power Settings | Treatment Duration (min) |
|---|---|---|---|---|
| Breast | Breast Adenocarcinoma (TNBC) | 3 | 120p | 6 |
| Breast | Breast Squamous Cell Carcinoma (TNBC) | 3 | 120p | 7 |
| Breast | Breast Adenocarcinoma (ER+ PR+) | 3 | 120p | 6 |
| Breast | Breast Ductal Carcinoma (ER+ PR+) | 3 | 120p | 6 |
| Breast | Breast Ductal Carcinoma (TPBC) | 3 | 120p | 6 |
| Breast | Breast Adenocarcinoma (HER2+) | 3 | 120p | 5 |
| Colon | Colorectal Carcinoma | 3 | 80p | 4 |
| Esophagus | Esophageal Squamous Cell Carcinoma | 3 | 120p | 7 |
| Esophagus | Esophageal Carcinoma (Barrett's) | 3 | 120p | 5 |
| Stomach | Gastric Adenocarcinoma | 3 | 120p | 8 |
| Kidney | Renal Adenocarcinoma | 3 | 80p | 3 |
| Liver | Cholangiocarcinoma | 3 | 120p | 8 |
| Ovary | Ovarian Adenocarcinoma | 3 | 120p | 5 |
| Pancreas | Pancreas Adenocarcinoma | 3 | 80p | 5 |
| Soft Tissue | Connective Tissue Fibrosarcoma | 3 | 120p | 8 |
| Soft Tissue | Synovial Sarcoma | 3 | 120p | 7 |
| Muscle | Muscle Rhabdomyosarcoma | 3 | 120p | 8 |
| Fat | Liposarcoma | 3 | 120p | 7 |

FIG. 7B

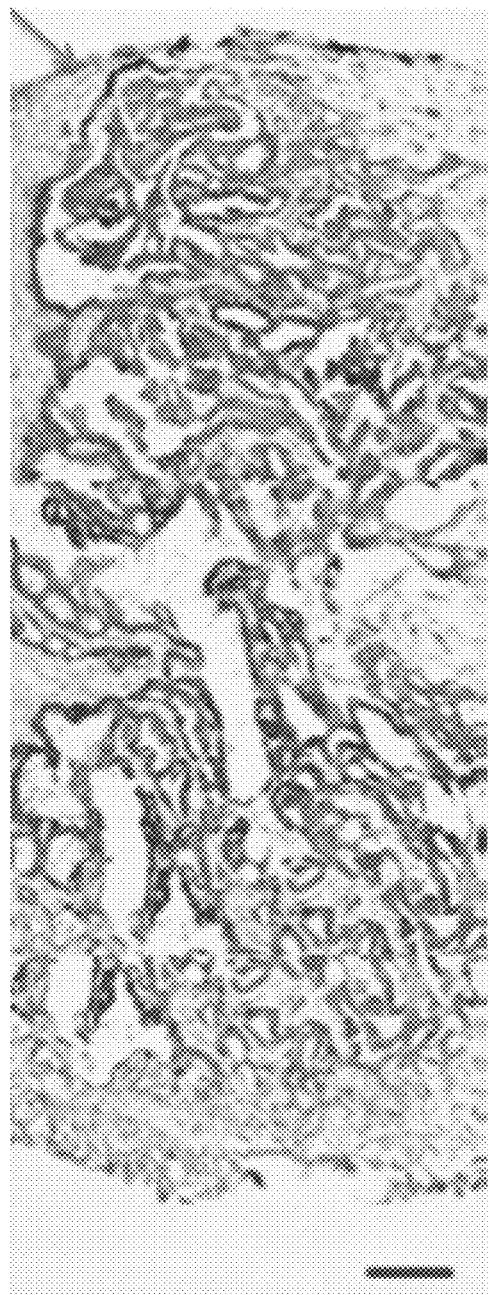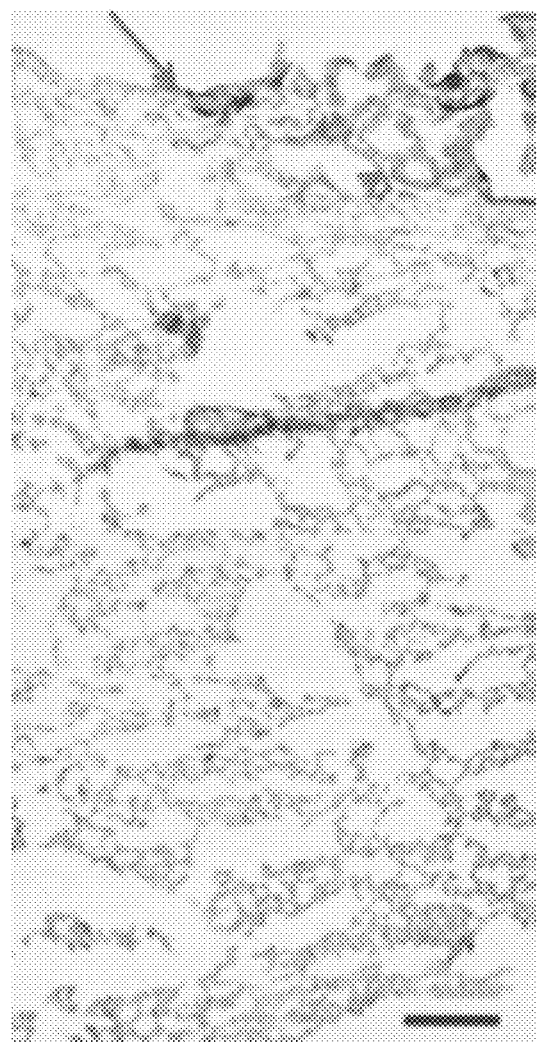
500μm
500μm
FIG. 12A
FIG. 12B 17 day explant culture 17 day isolated cell culture culture 20 day isolated cell culture culture 27 day isolated cell culture culture 200 μm
17 day isolated cell culture culture 200 μm
20 day isolated cell culture culture 200 μm
27 day isolated cell culture culture 200 μm
27 day isolated cell culture culture

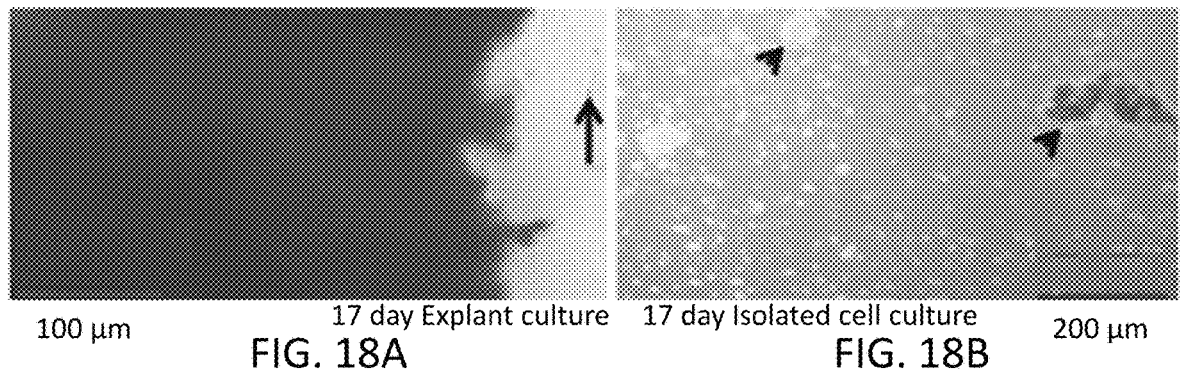
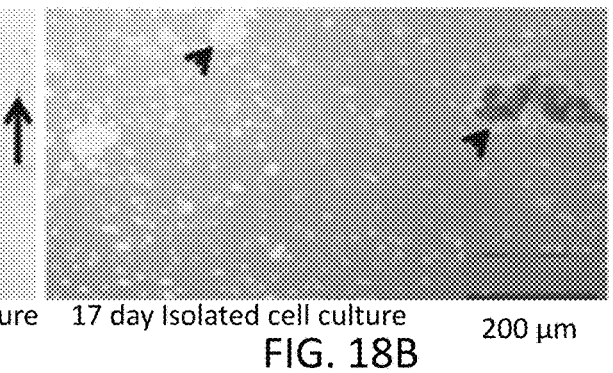
100 μm     17 day Explant culture    17 day Isolated cell culture    200 μm
FIG. 18A            FIG. 18B
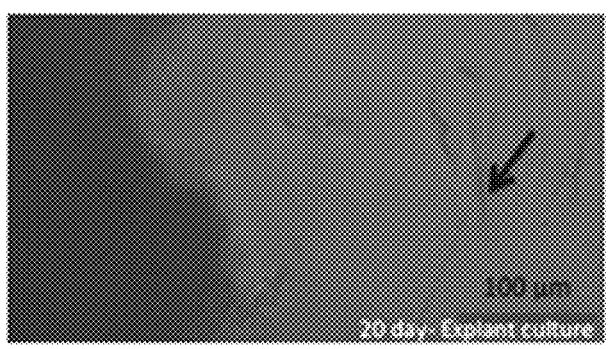
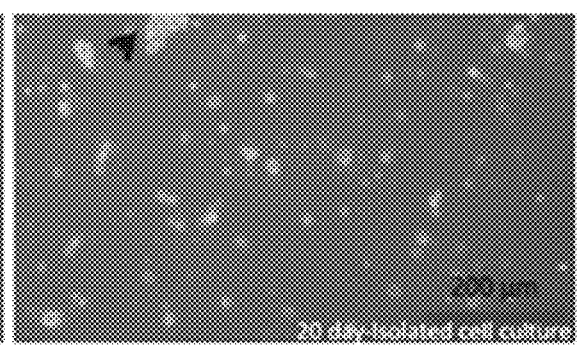
FIG. 18C            FIG. 18D
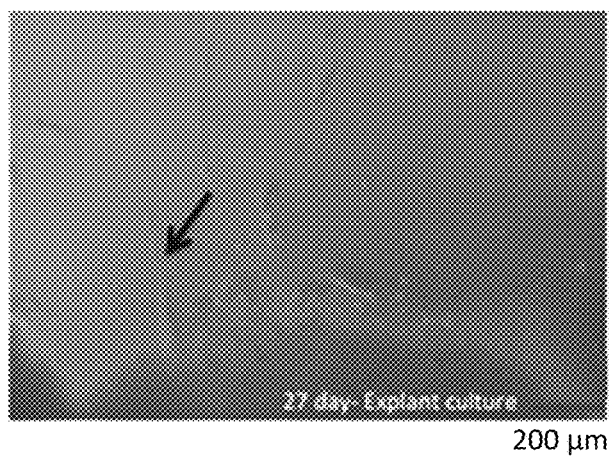
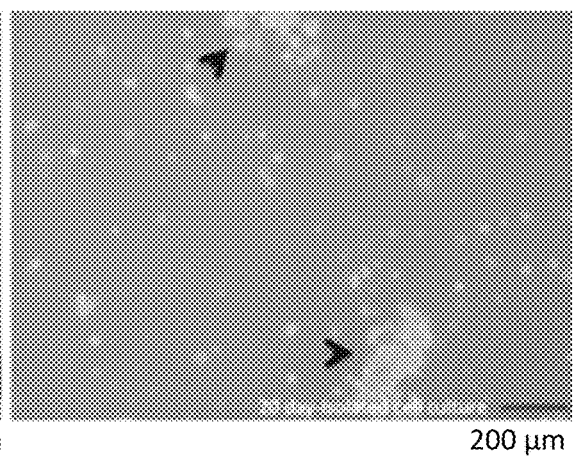
200 μm                                 200 μm
FIG. 18E            FIG. 18F

|  | %Double positive cells | Ki67% positive cells | %Trail-r1 positive cells | %DAPI positive cells |
|---|---|---|---|---|
| Colon tumor cells without CAP* | 24 | 16 | 32 | 28 |
| Colon tumor cells with CAP | NIL | NIL | NIL | 24 disintegrating cells |

FIG. 21

SYSTEM AND METHOD FOR COMBINATION OF COLD ATMOSPHERIC PLASMA TREATMENT WITH RADIATION AND CHEMOTHERAPY

CROSS-REFERENCE TO RELATED APPLICATIONS

The present application claims the benefit of the filing date of U.S. Provisional Patent Application Ser. No. 62/876,355 filed by the present inventors on Jul. 19, 2019.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for treating colon cancer with cold atmospheric plasma.

Brief Description of the Related Art

Colorectal cancer (CRC) is the third most common cancer in the world and the second leading cause of cancer death in the United States. In 2012 an estimated 103,170 new cases of colon cancer and approximately 40,290 rectal cases were newly diagnosed with 51,690 related deaths from these combined cancers. See, Siegel R, Naishadham D, Jemal A. Cancer statistics, 2012. CA Cancer J Clin. 2012; 62:10-29. There is evidence of peritoneal carcinomatosis (PC) in 8-10% of these patients at the time of diagnosis and 25% during the progression of their disease. See, Chu D Z, Lang N P, Thompson C, Osteen P K, Westbrook K C. Peritoneal Carcinomatosis in non-gynecologic malignancy. Cancer. 1989; 63:364-7; Sadeghi B, Arvieux C, Glehen O, et al. Peritoneal carcinomatosis from non-gynecologic Smalignancies. Results from the EVOCAPE 1 multicentric prospective study. Cancer. 2000; 88:358-63; Glehen O, Osinky D, Cotte E, Kwiatkowski F, Freyer G, Issac S, Trillet-lenoir V, Sayagbeaujard AC, Francois Y, Vignal J, et al. Intraperitoneal chemohyperthermia using a closed abdominal procedure and cytoreductive surgery for the treatment of peritoneal carcinomatosis: morbidity and mortality analysis of 216 consecutive procedures. Ann Surg Oncol. 2003; 10(8):863-9; and Glockzin G, Rochon J, Arnold D, Sa L, Klebl F, Zeman F, Koller M, Schlitt H J, Piso P. A prospective multicenter phase II study evaluating multimodality treatment of patients with peritoneal carcinomatosis arising from appendiceal and colorectal cancer: the combatac trial. BMC Cancer. 2013; 13:67.

PC is associated with a poor prognosis. Patients are considered to have a terminal condition with a 6-10 month median survival time See, Jayne D G, Fook S, Loi C, Seow-Choen F. Peritoneal carcinomatosis from colorectal cancer. Br J Surg. 2002; 89:1545-50; and Piso P, Arnold D. Multimodal treatment approaches for peritoneal carcinosis in colorectal cancer. Dtsch Arztebl Int. 2011; 108(47):802-8. The standard treatment for advanced stage CRC and PC is systemic chemotherapy which is considered palliative with minimal improvement in patient survival. Advanced chemotherapeutic regimens such as FOLFOX have been reported to improve survival to a median of 15.7 months See, Kulu Y, Muller-stich B, Buchler M W, Ulrich A. Surgical treatment of peritoneal carcinomatosis: current treatment modalities. Langenbeck's Arch Surg. 2013; 399(1):41-53; and Franko J, Shi Q, Goldman C D, et al. Treatment of Colorectal peritoneal carcinomatosis with systemic chemotherapy: a pooled analysis of north central cancer treatment group phase III trials n9741 and n9841. J Clin Oncol. 2012; 30:263-7.

Cytoreductive surgery (CRS) combined with hyperthermic intraoperative peritoneal chemotherapy (HIPEC) has evolved over the past 20 years as a new approach for the treatment of PC. CRS is described as removal of gross tumor follow by HIPEC treatment. Despite limited evidence to support CRS and HIPEC, there are some reports that this new approach has reported beneficial results. See, Verwaal V J, van Ruth S, de Bree E, et al. Randomized trial of cytoreduction and hyperthermic intraperitoneal chemotherapy versus systemic chemotherapy and palliative surgery in patients with peritoneal carcinomatosis of colorectal cancer. J Clin Oncol. 2003; 21:3737-43. Although there are promising results, CRS and HIPEC is associated with a significant morbidity, mortality, increase operating time, prolonged ICU care which results in an increase cost in patient care. This new multimodality approach is limited to several factors; age, extra abdominal disease (liver or lung metastasis), and peritoneal cancer index (PCI) which is the most common prognostic indicator and relies on the spread of the disease based on a scoring systems and the capability of complete removal of the gross tumor. PCI score calculates the spread of tumor in 13 areas of the abdomen in combination with tumor size. It ranges from 0 to 39 points. An elevated score indicates significant increase tumor load. See, Riss S, Mohamed F, Dayal S, Cecil T, Stift A, Bachleitner-Hofmann T, Moran B. Peritoneal Metasases from colorectal cancer: patient selection for cytoreductive surgery and Hyperthermic Intraperitoneal chemotherapy. Eur J Surg Oncol. 2013; 39 (9):931-7. Elias et al. (See, Elias D, Gilly F, Quenet F, et al. Peritoneal colorectal carcinomatosis treated with surgery and Perioperative Intraperitoneal Chemotherapy: Retrospective analysis of 523 patients from a multicentric French study. J Clin Oncol. 2010; 28:63-8) reported a 4-year survival rate of 44% if the PCI score is <6, score between 7 and 12 (22%) and >19 (7%) respectively. CRS and HIPEC is not recommended if the PCI score is >20. Controversy still exists whether CRS and HIPEC is considered "experimental."

Recent progress in atmospheric plasmas led to creation of cold plasmas with ion temperatures close to room temperature. Cold non-thermal atmospheric plasmas can have tremendous applications in biomedical technology. K. H. Becker, K. H. Shoenbach and J. G. Eden "Microplasma and applications" *J. Phys. D.: Appl. Phys.* 39, R55-R70 (2006). In particular, plasma treatment can potentially offer a minimum-invasive surgery that allows specific cell removal without influencing the whole tissue. Conventional laser surgery is based on thermal interaction and leads to accidental cell death i.e. necrosis and may cause permanent tissue damage. In contrast, non-thermal plasma interaction with tissue may allow specific cell removal without necrosis. In particular, these interactions include cell detachment without affecting cell viability, controllable cell death etc. It can be used also for cosmetic methods of regenerating the reticular architecture of the dermis. The aim of plasma interaction with tissue is not to denaturate the tissue but rather to operate under the threshold of thermal damage and to induce chemically specific response or modification. In particular presence of the plasma can promote chemical reaction that would have desired effect. Chemical reaction can be promoted by tuning the pressure, gas composition and energy. Thus, the important issues are to find conditions that produce effect on tissue without thermal treatment. Overall plasma treatment offers the advantage that is can never be thought of in most advanced laser surgery. E. Stoffels, I. E Kieft, R. E. J Sladek, L. J. M van den Bedem, E. P van der Laan, M. Steinbuch "Plasma needle for in vivo medical treatment: recent developments and perspectives" Plasma Sources Sci. Technol. 15, S169-S180 (2006).

Plasma medicine has qualified as a new scientific field after intense research effort in low-temperature or cold atmospheric plasma applications. See, Laroussi M, Kong M, Morfill G, Stolz W, editors. Plasma medicine. Cambridge; 2012; Friedman A, Friedman G. Plasma medicine. Hoboken: Wiley; 2013; and Keidar M, Beilis II. Plasma Engineering: application in aerospace, nanotechnology and bionanotechnology. Oxford: Elsevier; 2013. It is known that cold atmospheric plasmas (CAP) produce various chemically reactive species including reactive oxygen species (ROS) and reactive nitrogen species (RNS). CAP is a cocktail containing ROS and RNS in combination with transient electric fields, UV and charged species.

CAP has already been proven to be effective in wound healing, skin diseases, hospital hygiene, sterilization, antifungal treatments, dental care, and cosmetics targeted cell/tissue removal. See, Morfill GE, Kong MG, Zimmermann JL. Focus on plasma medicine. Review. New J Phys. 2009; 11:115011; Keidar M. Plasma for cancer treatment. Plasma Source Sci Technol. 2015; 24:033001; and Fridman G, Friedman G, Gutsol A, Shekhter A B, Vasilets V N, Fridman A. Applied plasma medicine. Plasma Process Polym. 2008; 5:503. One of the most recent applications of CAP is in cancer therapy. See, Vandamme M, Robert E, Pesnel S, Barbosa E, Dozias S, Sobilo J, Lerondel S, Le Pape A, Pouvesle J M. Antitumor effect of plasma treatment on U87 Glioma Xenografts: preliminary results. Plasma Process Polym. 2010; 7:264; Keidar M, Walk R, Shashurin A, Srinivasan P, Sandler A, Dasgupta S, Ravi R, Guerrero-Preston R, Trink B. Cold plasma selectivity and the possibility of a paradigm shift in cancer therapy. Br J Cancer. 2011; 105:1295; and Vandamme M, Robert E, Lerondel S, Sarron V, Ries D, Dozias S, Sobilo J, Gosset D, Kieda C, Legrain B, Pouvesle J-M, Le Pape A. ROS implication in a new antitumor strategy based on non-thermal plasma. Int J Cancer. 2011; 130:2185. Multiple studies have convincingly demonstrated that the CAP treatment leads to selective eradication of cancer cells in vitro and reduction of tumor size in vivo. While most studies were done in vitro, some work was done in vivo. Recently, clinical cases of CAP application in cancer therapy were presented at the 2nd International Workshop on Plasma for Cancer Therapy in Nagoya (Japan) and one of these studies involving 12 patients afflicted with advanced squamous cell carcinoma of the head and neck has been documented in a recent paper. See, Metelmann HR. What kind of impact is possible by plasma-jet in head and neck cancer?", The 2nd International Workshop on Plasma for Cancer Treatment, Nagoya, Japan, March, 2015; Canady J. "Development and clinical application of hybrid and cold atmospheric plasma combined with systemic chemotherapy and selective 3D conformal radiation therapy: A novel approach to the treatment of peritoneal metastases from colorectal cancer." The $2^{nd}$ International Workshop on Plasma for Cancer Treatment, Nagoya, Japan, March, 2015; and Metelmann H R, Nedrelow D S, Seebauer C, Schuster M, von Woedtke T, Weltmann K-D, Kindler S, Metelmann P H, Finkelstein S E, Von Hoff D D, Podmelle F. Head and neck cancer treatment and physical plasma. Clin Plasma Med. 2015; 3:17-23.

Several different systems and methods for performing Cold Atmospheric Plasma (CAP) treatment have been disclosed. For example, U.S. Published Patent Application No. 2014/0378892 discloses a two-electrode system for CAP treatement. U.S. Pat. No. 9,999,462 discloses a converter unit for using a traditional electrosurgical system with a single electrode CAP accessory to perform CAP treatment.

As a near-room temperature ionized gas, cold atmospheric plasma (CAP) has demonstrated its promising capability in cancer treatment by causing the selective death of cancer cells in vitro. See, Yan D, Sherman J H and Keidar M, "Cold atmospheric plasma, a novel promising anticancer treatment modality," *Oncotarget.* 8 15977-15995 (2017); Keidar M, "Plasma for cancer treatment," *Plasma Sources Sci. Technol.* 24 33001 (2015); Hirst A M, Frame F M, Arya M, Maitland N J and O'Connell D, "Low temperature plasmas as emerging cancer therapeutics: the state of play and thoughts for the future," *Tumor Biol.* 37 7021-7031 (2016). The CAP treatment on several subcutaneous xenograft tumors and melanoma in mice has also demonstrated its potential clinical application. See, Keidar M, Walk R, Shashurin A, Srinivasan P, Sandler A, Dasgupta S, Ravi R, Guerrero-Preston R and Trink B, "Cold plasma selectivity and the possibility of a paradigm shift in cancer therapy," *Br. J. Cancer.* 105 1295-301 (2011); Vandamme M, Robert E, Dozias S, Sobilo J, Lerondel S, Le Pape A and Pouvesle J-M, "Response of human glioma U87 xenografted on mice to non thermal plasma treatment," *Plasma Med.* 1 27-43 (2011); Brulle L, Vandamme M, Ries D, Martel E, Robert E, Lerondel S, Trichet V, Richard S, Pouvesle J M and Le Pape A, "Effects of a Non thermal plasma treatment alone or in combination with gemcitabine in a MIA PaCa2-luc orthotopic pancreatic carcinoma model," *PLoS One.* 7 e52653 (2012); and Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," *Plasma Process. Polym.* 12 1400-1409 (2015).

The rise of intracellular reactive oxygen species (ROS), DNA damage, mitochondrial damage, as well as apoptosis have been extensively observed in the CAP-treated cancer cell lines. See, Ahn H J, Kim K II, Kim G, Moon E, Yang S S and Lee J S, "Atmospheric-pressure plasma jet induces apoptosis involving mitochondria via generation of free radicals,". *PLoS One.* 6 e28154 (2011); Ja Kim S, Min Joh H and Chung T H, "Production of intracellular reactive oxygen species and change of cell viability induced by atmospheric pressure plasma in normal and cancer cells," *Appl. Phys. Lett.* 103 153705 (2013); and Yan D, Talbot A, Nourmohammadi N, Sherman J H, Cheng X and Keidar M, "Toward understanding the selective anticancer capacity of cold atmospheric plasma—a model based on aquaporins (Review)," *Biointerphases.* 10 040801 (2015). The increase of intracellular ROS may be due to the complicated intracellular pathways or the diffusion of extracellular ROS through the cellular membrane. See, Yan D, Xiao H, Zhu W, Nourmohammadi N, Zhang L G, Bian K and Keidar M, "The role of aquaporins in the anti-glioblastoma capacity of the cold plasma-stimulated medium," *J. Phys. D. Appl. Phys.* 50 055401 (2017). However, the exact underlying mechanism is still far from clear.

Cancer cells have shown specific vulnerabilities to CAP. See, Yan D, Talbot A, Nourmohammadi N, Cheng X, Canady J, Sherman J and Keidar M, "Principles of using cold atmospheric plasma stimulated media for cancer treatment," *Sci. Rep.* 5 18339 (2015)

Understanding the vulnerability of cancer cells to CAP will provide key guidelines for its application in cancer treatment. Only two general trends about the cancer cells' vulnerability to CAP treatment have been observed in vitro based on just a few cell lines. First, one study just compared the cytotoxicity of CAP treatment on the cancer cell lines expressing p53 with the same treatment on the cancer cell lines without expressing p53.

The cancer cells expressing the p53 gene were shown to be more resistant to CAP treatment than p53 minus cancer cells. Ma Y, Ha C S, Hwang S W, Lee H J, Kim G C, Lee K W and Song K, "Non-thermal atmospheric pressure plasma preferentially induces apoptosis in p53-mutated cancer cells by activating ROS stress-response pathways," *PLoS One.* 9 e91947 (2014). p53, a key tumor suppressor gene, not only restricts abnormal cells via the induction of growth arrest or apoptosis, but also protects the genome from the oxidative damage of ROS such as $H_2O_2$ through regulating the intracellular redox state. Sablina A A, Budanov A V, Ilyinskaya G V, Larissa S, Kravchenko J E and Chumakov P M, "The antioxidant function of the p53 tumor suppressor," *Nat. Med.* 11 1306 (2005). P53 is an upstream regulator of the expression of many antioxidant enzymes such as glutathione peroxidase (GPX), glutaredoxin 3 (Grx3), and manganese superoxide dismutase (MnSOD). Maillet A and Pervaiz S, "Redox regulation of p53, redox effectors regulated by p53: a subtle balance," *Antioxid. Redox Signal.* 16 1285-1294 (2012). In addition, the cancer cells with a lower proliferation rate are more resistant to CAP than cancer cells with a higher proliferation rate. Naciri M, Dowling D and Al-Rubeai M, "Differential sensitivity of mammalian cell lines to non-thermal atmospheric plasma," *Plasma Process. Polym.* 11 391-400 (2014). This trend may be due to the general observation that the loss of p53 is a key step during tumorigenesis. Tumors at a high tumorigenic stage are more likely to have lost p53. See, Fearon E F and Vogelstein B, "A genetic model for colorectal tumorigenesis," *Cell.* 61 759-767 (1990).

Despite the complicated interaction between CAP and cancer cells, the initial several hours after treatment has been found to be an important stage for the cytotoxicity of CAP. The anti-cancer ROS molecules in the extracellular medium are completely consumed by cells during this time period. After the initial several hours, replacing the medium surrounding the cancer cells does not change the cytotoxicity of CAP. See, Yan D, Cui H, Zhu W, Nourmohammadi N, Milberg J, Zhang L G, Sherman J H and Keidar M, "The specific vulnerabilities of cancer cells to the cold atmospheric plasma-stimulated solutions," *Sci. Rep.* 7 4479 (2017).

SUMMARY OF THE INVENTION

In a preferred embodiment, the present invention is a novel treatment approach for peritoneal carcinomatosis secondary to colon cancer using Cold Atmospheric Plasma combined with chemotherapy, radiation and cytoreductive surgery.

In a preferred embodiment, the present invention is a method for applying cold atmospheric plasma treatment to target tissue. The method comprises selecting through a graphical user interface a particular cancer cell line associated with target tissue, retrieving, with the computing device, settings data associated with the selected cancer cell line from a database of cell line data and associated settings data in a storage, and applying, with the computing device, the retrieved settings data to a cold atmospheric plasma system.

In another preferred embodiment, the method comprises generating a database of a plurality of cancer cell lines and optimum cold atmospheric plasma settings associated with each of the plurality of cancer cell lines, storing the database in a storage medium, selecting through a graphical user interface on a computing device a particular cancer cell line associated with the target tissue, retrieving, with the computing device, settings data from a database of cell line data and associated settings data in a storage, and applying, with the computing device, the retrieved settings data to a cold atmospheric plasma system. Further, the cold atmospheric plasma settings in the generated database may be based upon a predicted CAP effectiveness derived from testing the plurality of cancer cells lines with CAP treatment at a plurality of settings.

In yet another embodiment, the present invention is a method for treating cancer comprising the steps of pre-operatively performing at least one of radiation and chemotherapy to a patient having a cancerous solid tumor, performing intra-operative resection of at least a portion of said solid tumor, applying cold atmospheric plasma intra-operatively to margins surrounding the area from which the solid tumor was resected, and post-operatively performing at least one of radiation and chemotherapy to a patient having a cancerous solid tumor. The method further may comprise intra-operatively performing hyperthermic intraoperative peritoneal chemotherapy on said patient.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 4A is a block diagram of a preferred embodiment of pressure control system of a gas-enhanced electrosurgical generator in accordance with the present invention configured to perform an argon-enhanced electrosurgical procedure.

FIG. 4B is a block diagram of a preferred embodiment of pressure control system of a gas-enhanced electrosurgical generator in accordance with the present invention configured to perform a cold atmospheric plasma procedure.

FIG. 7B is a table of exemplary settings for performing CAP treatment on various types of cancer.

FIGS. 12A and 12B are images of H&E stained sections showing (FIG. 12A) Metastatic liver treated with cold plasma (FIG. 12B) without Cold Plasma treatment, along the thickness of the sample excised from the patient.

FIGS. 18A-18F are images showing in vitro expansion of Human Colon Cancer cells from Sub phrenic Diaphragm samples treated with CAP. Explant (a, c, e) and isolated cell cultures (b, d, f) of colon cells from Sub phrenic Diaphragm showing cell death and many floating dead cells (arrowhead) in the presence of CAP after 17-27 days in culture. Arrow shows fibroblast-like cells from the tissue explants.

FIG. 21 is a table illustrating characterization of cellular profile of human colon cancer cells expanded in vitro. The entire culture dish was analyzed to calculate proportion of total number of cells. Significant (*p<0.05) difference in the profile was cells with CAP treatment and without treatment was observed. Note the absence of TRAIL-R1 and Ki67 positivity in CAP treated samples.

DETAILED DESCRIPTION OF THE PREFERRED EMBODIMENTS

Figure 1:
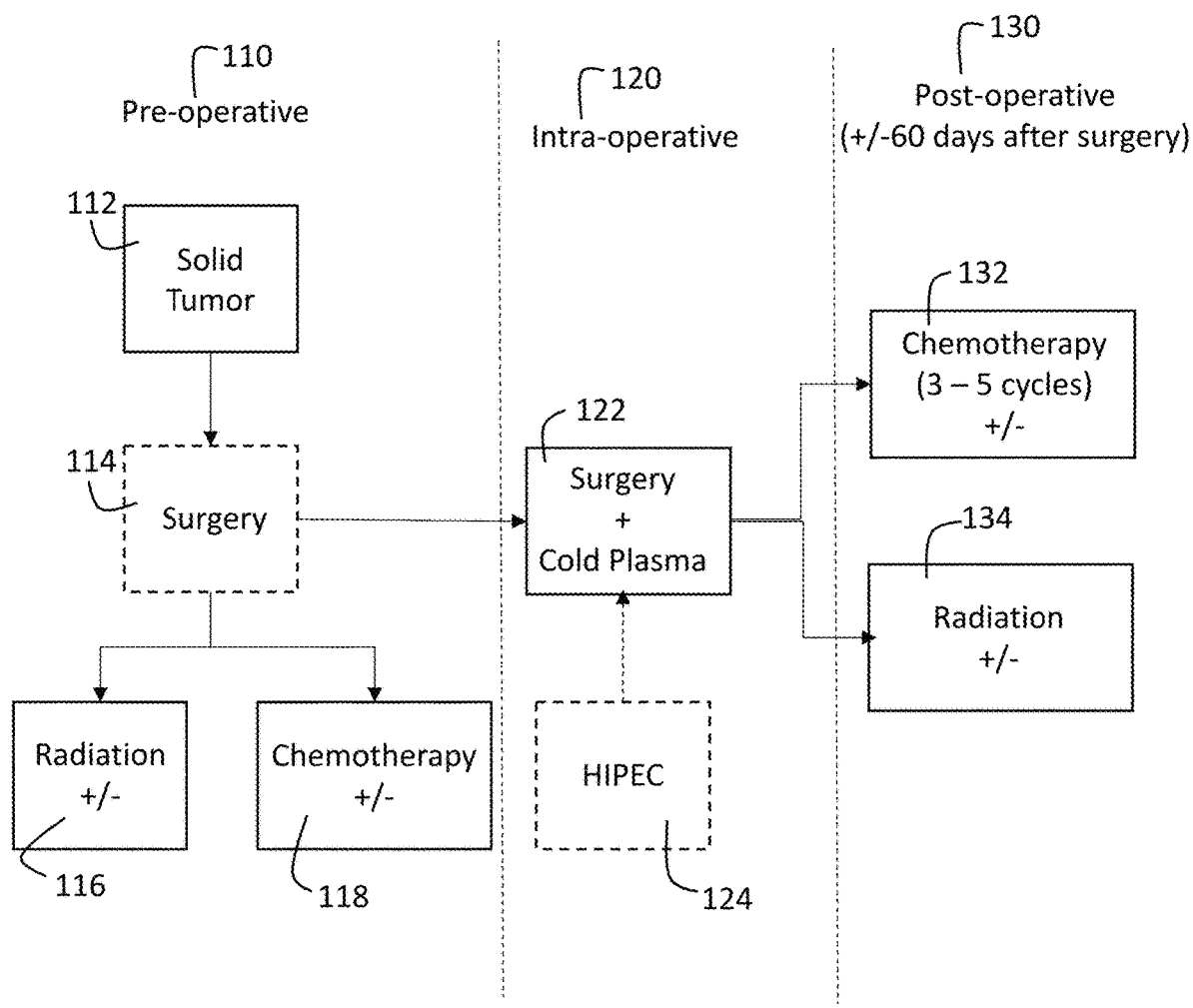
FIG. 1 is a flow chart illustrating steps of a procedure for performing a cold atmospheric plasma treatment of cancer cells in combination with chemo-radiation and cytoreductive surgery in accordance with a preferred embodiment of the present invention.

A procedure for performing a cold atmospheric plasma treatment of cancer cells in combination with chemo-radiation and cytoreductive surgery in accordance with a preferred embodiment of the present invention is described with reference to FIG. 1. Three stages of treatment are shown: (1) pre-operative 110, intra-operative 120 and post-operative 130. Pre-operative, the patient has a cancerous solid tumor 112. In some instances, the cancer may be a recurrence, in which the patient previously may have had surgery 114 to re-move the tumor. The patient may undergo pre-operative radiation 116 or chemotherapy 118. Intra-operative, surgery is performed to resect the solid tumor (cytopreduction) and cold atmospheric plasma is applied to the margins of the resected area 122. Further, additional treatments, such as intraperitoneal hyperthermic chemoperthrapy (HIPEC) may be performed 124. Intraperitoneal hyperthermic chemoperfusion (HIPEC) is a type of hyperthermia therapy used in combination with surgery in the treatment of advanced abdominal cancers. In this procedure, warmed anti-cancer medications are infused and circulated in the peritoneal cavity for a short period of time. The chemotherapeutic agents generally infused during IPHC are mitomycin-C and cisplatin. Post-operative, the patient may under further radiation 134 and chemotherapy 132. Other types of cancer therapies, such as tumor treating fields as described in U.S. Pat. No. 8,019,414, additionally can be used post-operatively with the present invention.

Figure 2A:
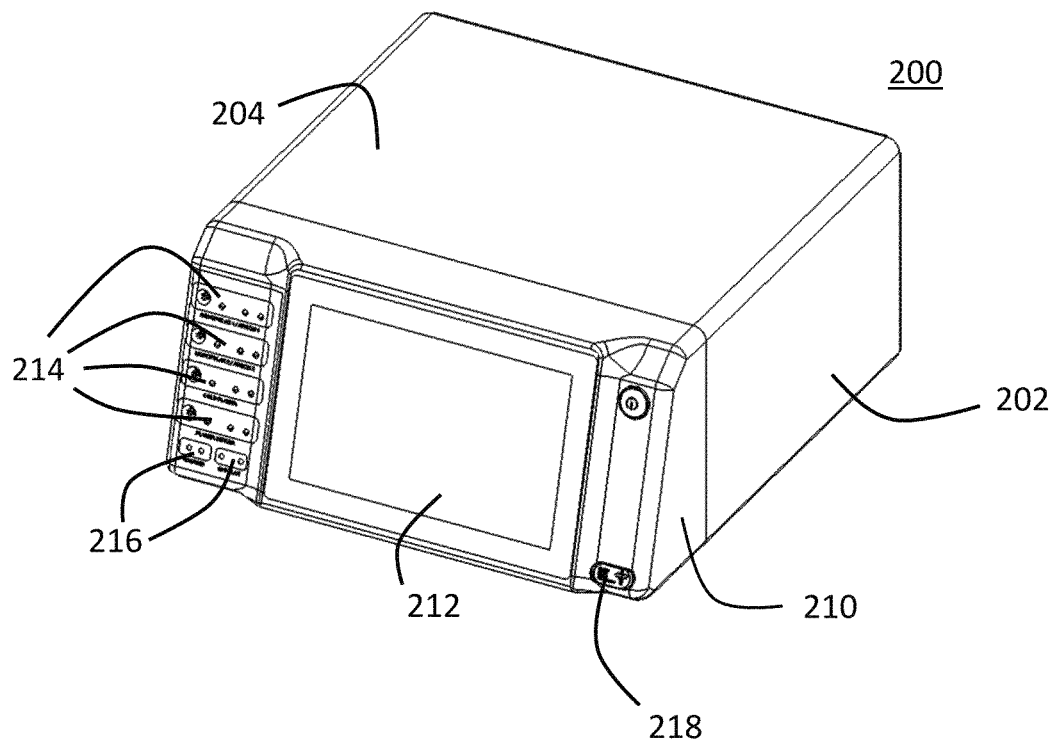
FIG. 2A is a perspective view of a preferred embodiment of a gas-enhanced electrosurgical generator that may be used in a preferred embodiment of the present invention.
Figure 2B:
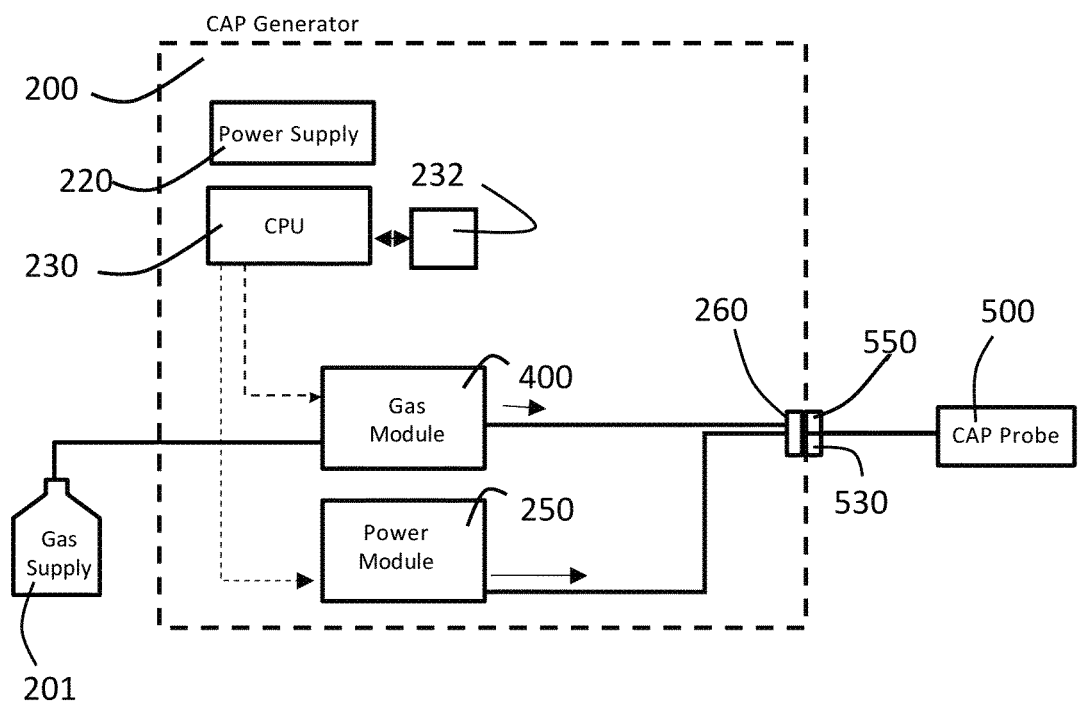
FIG. 2B is a block diagram of a cold atmospheric plasma generator in accordance with a preferred embodiment of the present invention.

A preferred embodiment of a CAP enabled generator is described with reference to the drawings. A gas-enhanced electrosurgical generator 200 in accordance with a preferred embodiment of the present invention is shown in FIGS. 2A-2B. As shown in FIG. 2A, the gas-enhanced generator has a housing 202 made of a sturdy material such as plastic or metal similar to materials used for housings of conventional electrosurgical generators. The housing 202 has a removable cover 204. The housing 202 and cover 204 have means, such as screws, tongue and groove, or other structure for removably securing the cover to the housing. The cover 204 may comprise just the top of the housing or multiple sides, such as the top, right side and left side, of the housing 202. The housing 202 may have a plurality of feet or legs (not shown) attached to the bottom of the housing. The bottom of the housing 202 may have a plurality of vents (not shown) for venting from the interior of the gas-enhanced generator.

A generator housing front panel 210 is connected to the housing 202. On the face front panel 210 there is a touchscreen display 212 and there may be one or a plurality of connectors 214 for connecting various accessories to the generator 200. For a cold atmospheric plasma generator such as is shown in FIG. 2B, for example, there is a connector 260 for connecting a cold atmospheric probe 500. An integrated multi-function electrosurgical generator, such as is shown in FIG. 3B the plurality of connectors may include an argon plasma probe, a hybrid plasma probe, a cold atmospheric plasma probe, or any other electrosurgical attachment. The face of the front panel 210 is at an angle other than 90 degrees with respect to the top and bottom of the housing to provide for easier viewing and use of the touch screen display 212 by a user.

Figure 5:
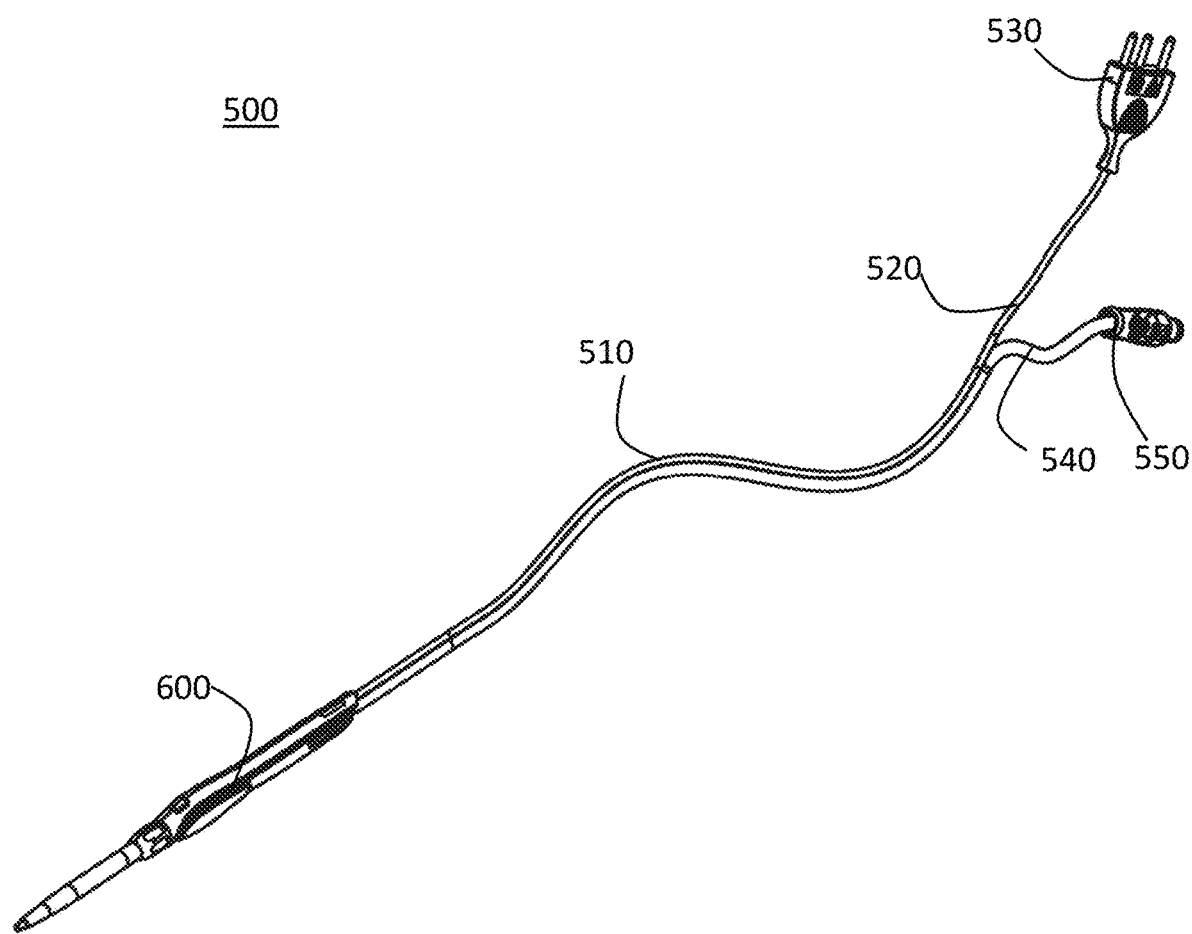
FIG. 5 is perspective view of a cold atmospheric plasma probe that may be used in a preferred embodiment of the present invention.
Figure 6A:
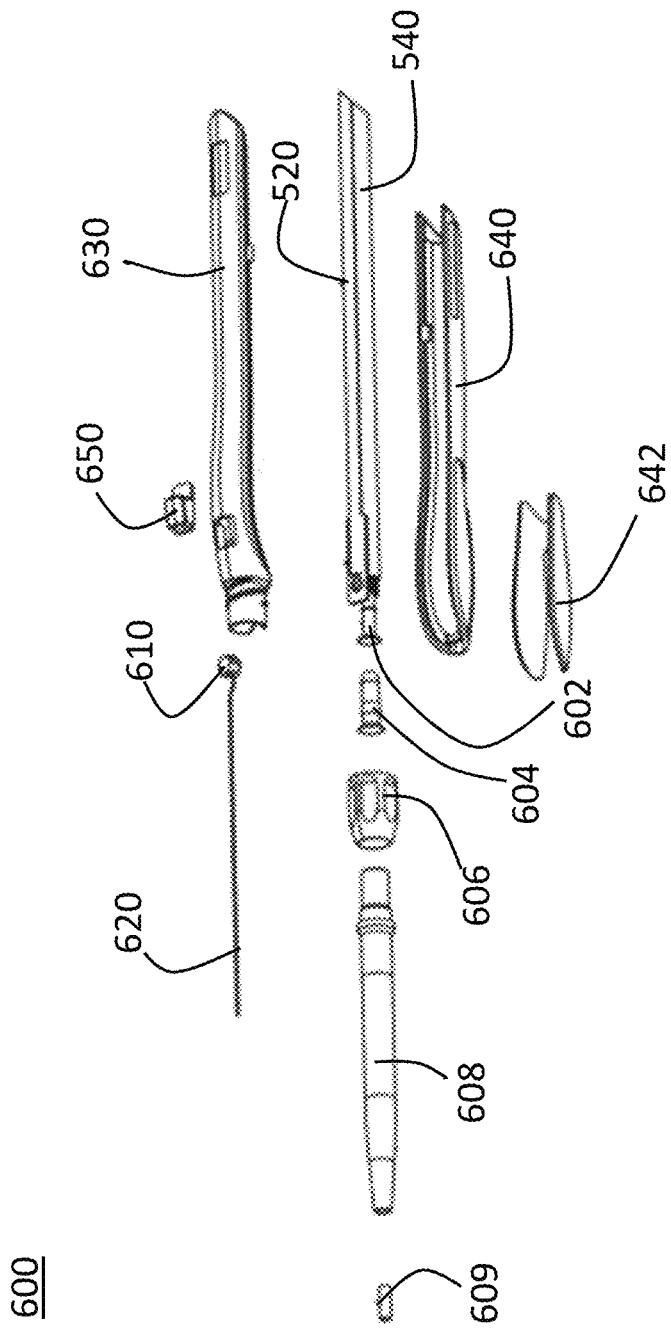
FIG. 6A is an assembly view of a handpiece of a cold atmospheric plasma probe that may be used in a preferred embodiment of the present invention.
Figure 6B:
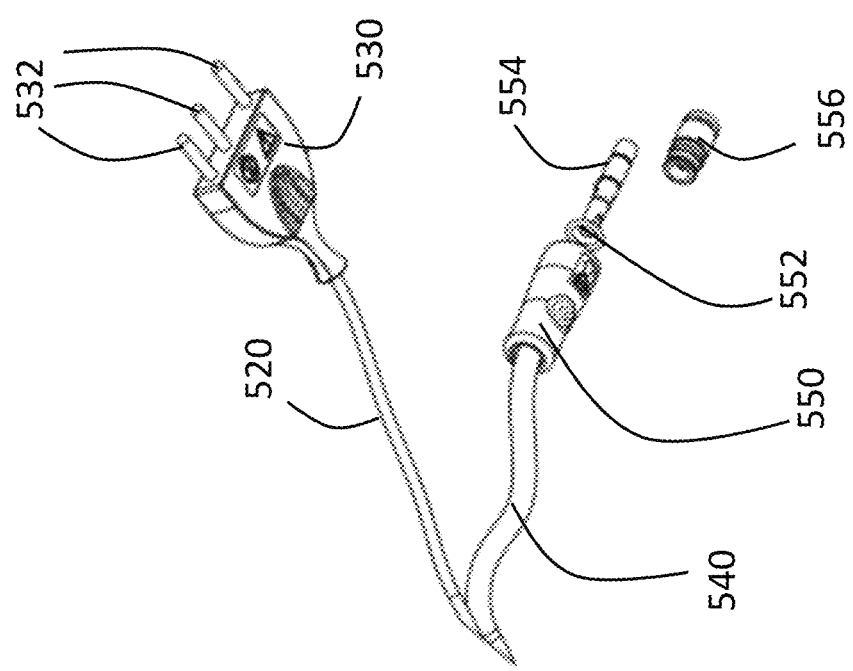
FIG. 6B is an assembly view of a cable harness of a cold atmospheric plasma probe that may be used in a preferred embodiment of the present invention.

As shown in FIG. 2B, an exemplary cold atmospheric plasma (CAP) generator 200 has a power supply 220, a CPU (or processor or FPGA) 230 and a memory or storage 232. The system further has a display 212 (FIG. 2A), which may be the display of a tablet computer. The CPU 230 controls the system and receives input from a user through a graphical user interface displayed on display 212. The CAP generator further has a gas control module 400 connected to a source 201 of a CAP carrier gas such as helium. The CAP generator 200 further has a power module 250 for generating low frequency radio frequency (RF) energy, such as is described in U.S. Pat. No. 9,999,462, which is hereby incorporated by reference in its entirety. The power module 250 contains conventional electronics and/or transformers such as are known to provide RF power in electrosurgical generators. The power module 250 operates with a frequency between 10-200 kHz, which is referred to herein as a "low frequency," and output peak voltage from 3 kV to 6 kV and preferably at a frequency near (within 20%) of 40 Hz, 100 Hz or 200 Hz. The gas module 400 and power module 250 are connected to connector 260 that allows for attachment of a CAP applicator 500 (as shown in FIGS. 5, 6A and 6B) to be connected to the generator 200 via a connector having an electrical connector 530 and gas connector 550.

As shown in FIG. 3B, other arrangements for delivery of the carrier gas and the electrical energy may be used with the invention. In FIG. 3B, an integrated CAP generator 300b is connected to a source 310 of a carrier gas (helium in this example), which is provided to a gas control system 400, which supplies the gas at a controlled flow rate to CAP applicator 500. A high frequency (HF) power module 340b supplies high frequency (HF) energy to a low frequency power module (converter) 350b, which outputs electrical energy having a frequency in the range of 10 kHz to 200 kHz and an output voltage in the range of 3 kV to 6 Kv. This type of integrated generator will have both a CAP connector 360b for connecting a CAP applicator or other CAP accessory and a connector 370b for attaching HF electrosurgical attachments such as an argon plasma or hybrid plasma probe (not shown).

Figure 3A:
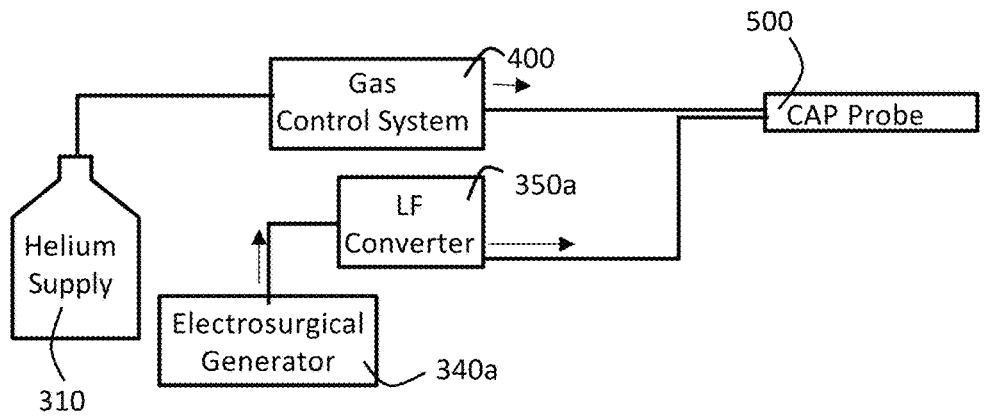
FIG. 3A is a block diagram of an embodiment of a cold atmospheric plasma system with an electrosurgical generator and a low frequency converter for producing cold plasma.
Figure 3B:
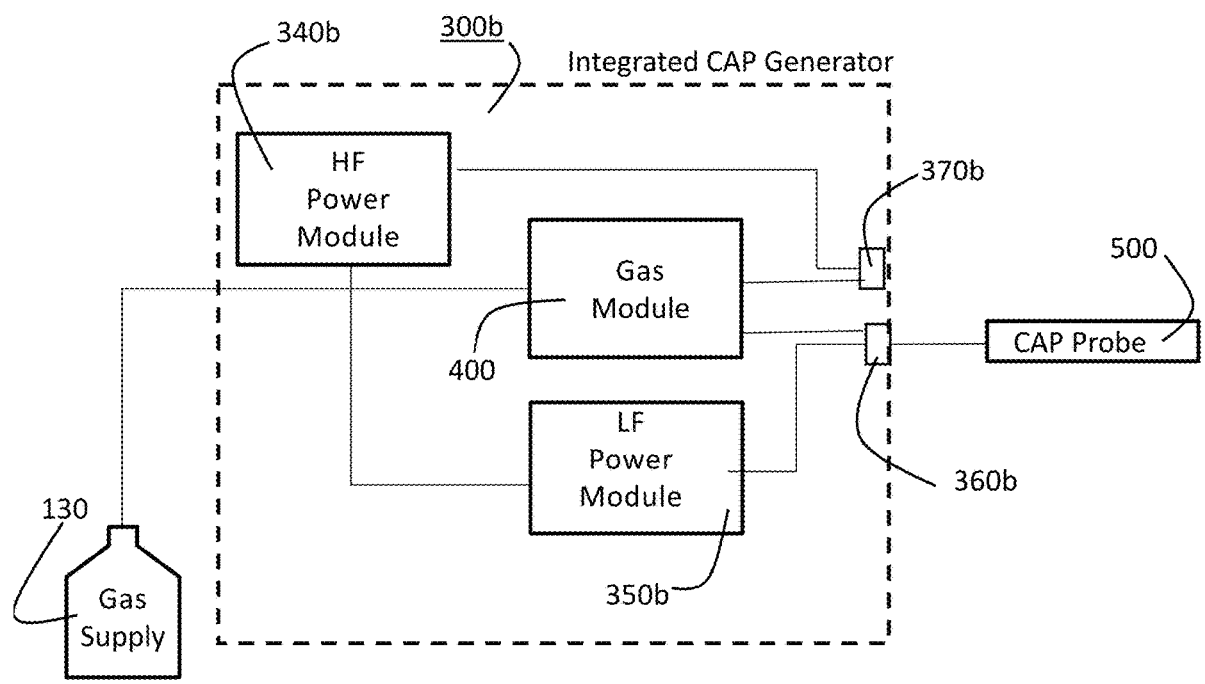
FIG. 3B is a block diagram of an embodiment of an integrated cold atmospheric plasma system that can perform multiple types of plasma surgeries.

Another embodiment, shown in FIG. 3A, has a carrier gas source 310 connected to a conventional gas control system 370, which in turn is connected to the CAP applicator 500, and a conventional electrosurgical generator 340 connected to a low frequency (LF) converter 350a, which is then connected to the CAP probe 500.

FIG. 4A is a schematic flow diagram illustrating the gas flow through the gas control module 400 and the method by which the module 400 controls the gas flow in accordance with a preferred embodiment of the present invention. As shown in FIG. 4A, the gas enters the gas control module at an inlet port (IN) 401 and proceeds to first solenoid valve (SV1) 410, which is an on/off valve. In an exemplary embodiment, the gas enters the gas module at a pressure of 75 psi. The gas then proceeds to a first pressure sensor (P1) 420, to a first pressure regulator (R1) 430. In an exemplary embodiment, the first pressure regulator (R1) 430 reduces the pressure of the gas from 75 psi to 18 psi. After the pressure regulator (R1) 430, the gas proceeds to flow sensor (FS1) 440, which senses the flow rate of the gas. Next, the gas proceeds to proportional valve (PV1) 450, which permits adjustment of a percentage of the opening in the valve. The gas then proceeds to a second flow sensor (FS2) 460, which senses the flow rate of the gas. This second flow sensor (FS2) 460 provides redundancy and thus provides greater safety and accuracy in the system. Next the gas proceeds to a second solenoid valve (SV2) 470, which is a three-way valve that provides for a vent function that can allow gas to exit the module through a vent 472. The gas then proceeds to a second pressure sensor (P2) 480, which provides a redundant pressure sensing function that again produces greater safety and accuracy of the system. Finally, the gas proceeds to a third solenoid valve (SV3) 490, which is a two-way on/off valve that is normally closed and is the final output valve in the module. The gas exits the module at an output port (OUT) 499, which is connected to tubing or other channel that provides a passageway for the gas to flow to an accessory connected to the electrosurgical unit.

FIG. 4B is a schematic flow diagram of an alternate embodiment of a gas control module illustrating the gas flow through the gas control module 400a and the method by which the module 400a controls the gas flow in accordance with a preferred embodiment of the present invention. As shown in FIG. 4B, the gas enters the gas control module at an inlet port 401a and proceeds to a first pressure regulator (R1) 430a. In an exemplary embodiment, the first pressure regulator (R1) 430a reduces the pressure of the gas from about 50-100 psi to 15-25 psi. After the pressure regulator (R1) 430a, the gas proceeds to a first pressure sensor (P1) 420a and then to a first solenoid valve (SV1) 410a, which is an on/off valve. Next, the gas proceeds to proportional valve (PV1) 450a, which permits adjustment of a percentage of the opening in the valve. Next, the gas proceeds to flow sensor (FS1) 440a, which senses the flow rate of the gas. Next the gas proceeds to a second solenoid valve (SV2) 470a, which is a three-way valve that provides for a vent function that can allow gas to exit the module through a vent 472a. The gas then proceeds to a second flow sensor (FS2) 460a, which senses the flow rate of the gas. This second flow sensor (FS2) 460a provides redundancy and thus provides greater safety and accuracy in the system. The gas then proceeds to a second pressure sensor (P2) 480a, which provides a redundant pressure sensing function that again produces greater safety and accuracy of the system. The gas exits the module at and output port 499a, which is connected to tubing or other channel that provides a passageway for the gas to flow to an accessory connected to the electrosurgical unit.

The various valves and sensors in either embodiment of the module are electrically connected to a main PCB Board through a connector. The PCB connector is connected to a PCB Board that has a microcontroller (such as CPU). As previously noted, a plurality of gas modules can be in a single gas control unit or single electrosurgical generator to provide control of multiple differing gases. The plurality of gas control modules further may be connected to the same PCB Board, thus providing common control of the modules.

In the above-disclosed embodiment, a cold atmospheric plasma below 35° C. is produced. When applied to the tissue surrounding the surgical area, the cold atmospheric plasma induces metabolic suppression in only the tumor cells and enhances the response to the drugs that are injected into the patient.

The cold plasma applicator 500 may be in a form such as is disclosed in U.S. Pat. No. 10,405,913 and shown in FIGS. 5, 6A and 6B. A hand piece assembly 600 has a top side piece 630 and a bottom side piece 640. A control button 650 extends from the interior of the hand piece through an opening in the top side piece 630. Within the hand piece 600 is body connector funnel 602, PCB board 608, electrical wiring 520 and hose tubing (PVC medical grade) 540. The wiring 520 and hose tubing 540 are connected to one another to form a wire and tubing bundle 510. A grip over mold 642 extends over the bottom piece portion 640. In other embodiments, a grip may be attached to the bottom piece 640 in other manners. A probe or scalpel assembly is attached to the end of the hand piece. The probe assembly has non-bendable telescoping tubing 606, a ceramic tip 609, a column nut or collet 606 and body connector tubing 604. The hose tubing 540 extends out of the proximal end of the hand piece to a body gas connector 550, which has an O-ring 552, gas connector core 554 and gas connector tip 556 for connecting to a connector on a gas-enhanced electrosurgical generator. The printed circuit board 608 connects to electrical wiring 520 which leads to electrical connector 530 having electrical pins 532. Inside the handpiece 600 is an electrode 620 and conductive connector 610. There is a control button 650 for controlling the application of electrical energy.

While the present application discloses a specific type of cold plasma, other types of plasma jets may be used in the present invention.

Cancer cell lines can be tested at varying settings or dosages of the CAP treatment to provide an estimate of which CAP treatment settings or dosages will provide the greatest effect on particular cell lines. In a preferred embodiment of the present invention, the results of such testing are used to generate a database of cancer cell lines with associated predicted optimum settings or dosage data and optionally effectiveness data. This database can be stored in memory or other storage in a CAP capable electrosurgical system or can be in an external storage, for example, accessible through a server or cloud computing system that can be accessed by a CAP capable electrosurgical system. The CAP capable electrosurgical system may have a graphical user interface that allows a user to enter an identifier for a particular cancer cell line into the user interface and thereby have the CAP enabled electrosurgical system automatically select the predicted optimum settings or dosage for that particular cancer cell line. The user can then perform a CAP treatment of target cancer cells at those predicted optimum settings.

Figure 7A:
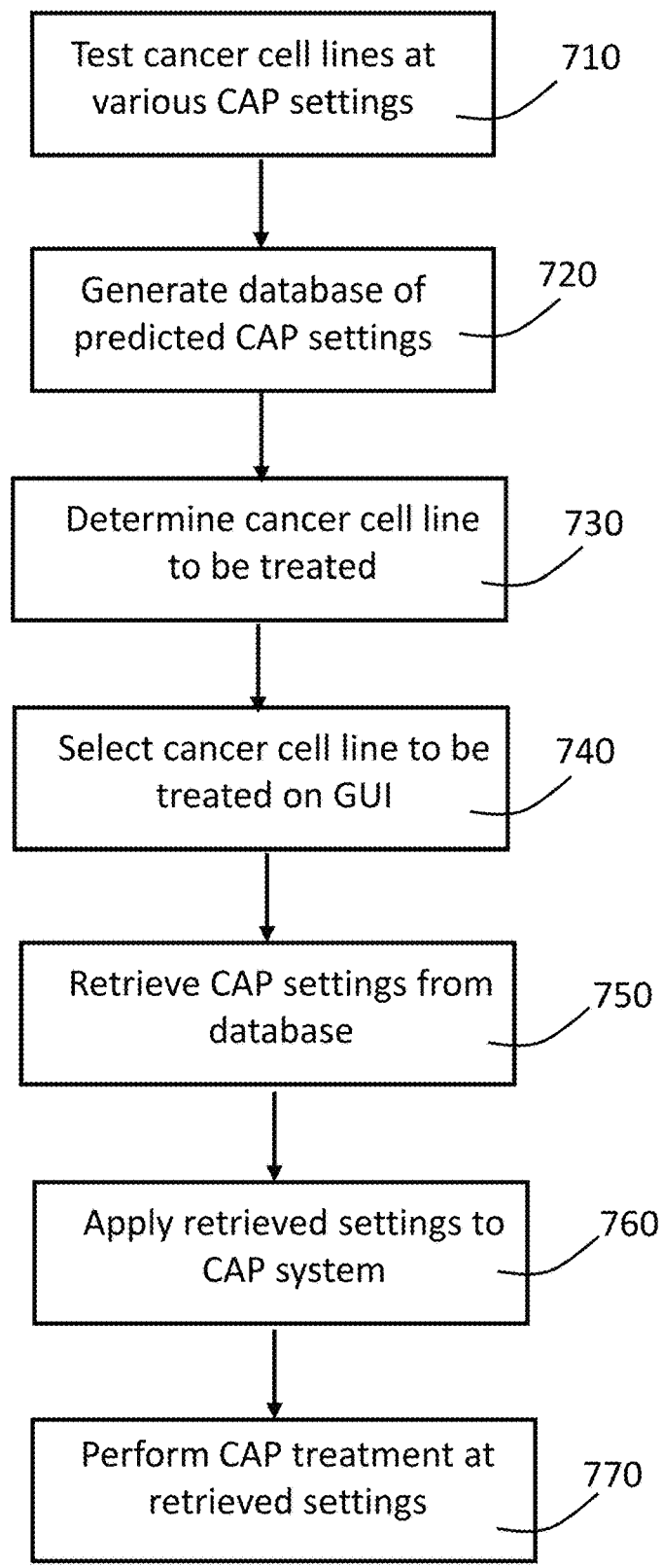
FIG. 7A is a flow chart of a method for performing CAP treatment in accordance with a preferred embodiment of the present invention.
Figure 8:
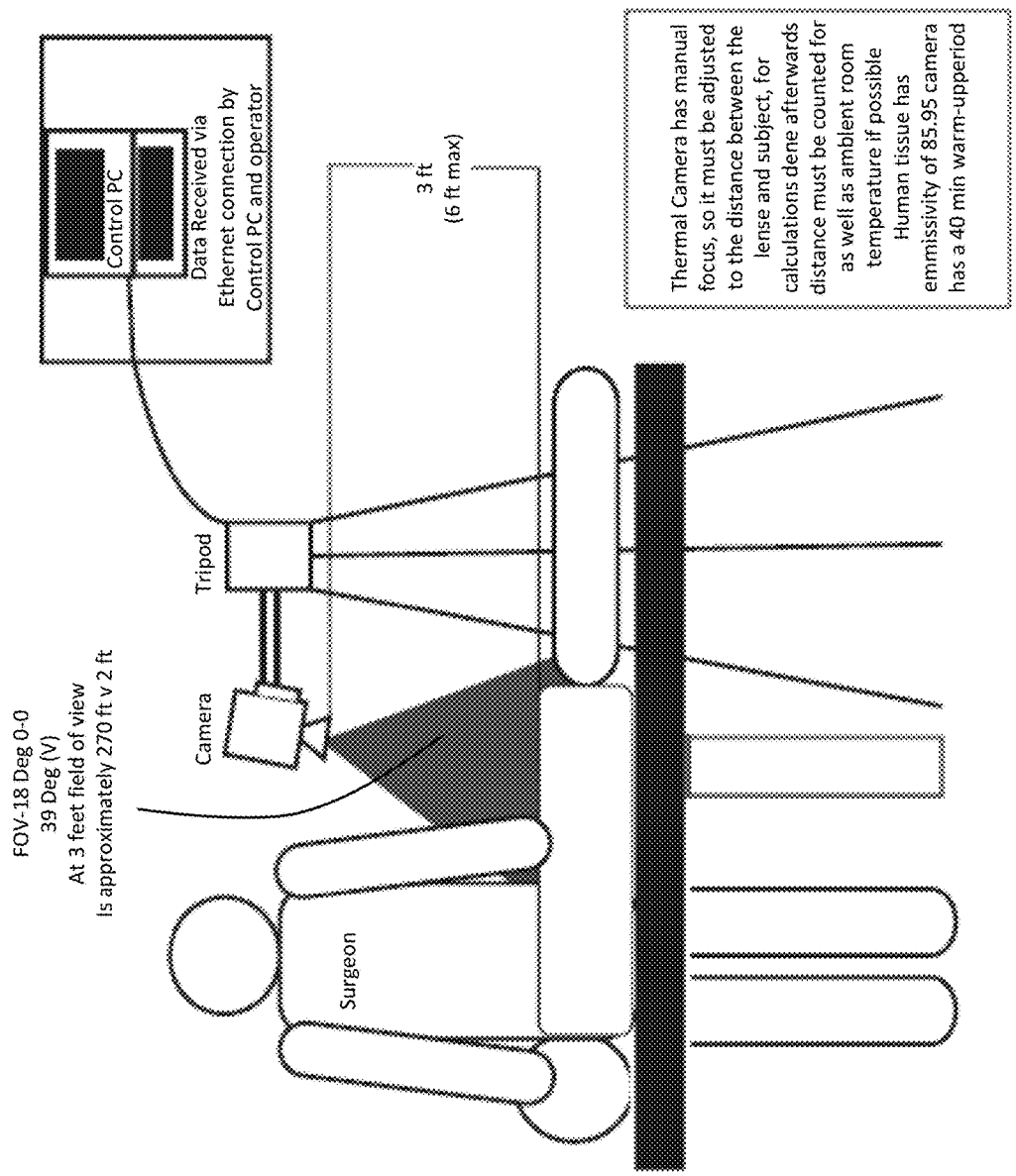
FIG. 8 is a diagram of an experimental setup for measuring body temperature during use of cold atmospheric plasma to treat cancer cells in a patient.

Thus, as shown in FIG. 7A, a method can be performed in which a plurality of cancer cell lines can be tested (step 710) to determine optimal treatment settings for that cell line. A database of cancer cell lines and associated CAP treatment data is generated and stored (step 720). Additional cancer cell line data and associate settings or dosage data can be added to the database as new cell lines are tested and new data is developed. A user performing a CAP treatment determines the particular cancer cell line to be treated (step 730) and then enters an identifier associated with a particular cancer cell line into a graphical user interface on a CAP capable electrosurgical system (step 740). The CAP capable electrosurgical system then accesses the stored database to retrieve CAP setting or dosages associated with the ID entered into the graphical user interface (step 750). The phrase "enter an identifier" used herein can mean any data entry or selection by the user that provides the graphical user interface with sufficient information to retrieve data from the database for a particular cell line. This could be selection from a list or menu, entry of an identifier through a physical or virtual keyboard associated with the system, scanning of a bar code, or any other means. Further, the graphical user interface and associated display do not need to physically be in the CAP capable generator but instead may be on external devices such as a tablet computing device that is in communication with the CAP enabled electrosurgical generator. The retrieved CAP settings are then applied to the CAP system (step 760). The user then can treat the target tissue with CAP at the preferred settings (step 770). The temperature of the cold plasma is less than 37° C. With the treatment, the temperature across the surface of the treated tissue decreases by 10-20° F. during treatment.

Example 1

Methods

SS-601 Electrosurgical generator integrated with Canady Plasma™ Coagulator and Canady Hybrid Plasma™ Scalpel (US Medical Innovations, LLC (USMI) Takoma Park, Md.) was used for gross dissection of tumor and afterwards the Canady Helios™ Cold Plasma Ablator (USMI Takoma Park, Md.) was used to treat the margins at the tumor site. The patient underwent exploratory laparotomy, liver segmentectomy, cholecystectomy, right partial diaphragm resection with reconstruction using alloderm patch, en bloc resection of distal small bowel, transverse, left colon, sigmoid colon, distal pancreas with spleen and omentum, small bowel resection, resection of tumors from the mesentery and abdominal wall and supracervical total abdominal hysterectomy with bilateral salpingoophorectomy. A R0 resection was completed. Time of procedure and estimated blood loss were 7.5 h and 800 cc respectively. Specimens sent to pathology were positive for metastatic adenocarcinoma from the liver, peritoneal implants, small bowel tumor with implants in the mesentery, bilateral tumor involvement adjacent to the ovaries, en bloc resection of the transverse, left and sigmoid colon, prior anastomosis to the small bowel, spleen with the tail of the pancreas, multiple tumor deposits of the mesentery, mesocolon, peripancreatic, perisplenic, adipose tissue and the small bowel prior anastomostic staple line. The patient's peritoneal cancer index (PCI) was >23 intra-operatively.

After surgery the patient was transferred to the ICU and subsequently transferred to the floor. Patient was taken back to the operating room seven days later for anastomotic leak at the ileoproctostomy site. Take down of the rectal anastomosis and Brook ileostomy was performed. Patient returned to the OR two days and five days later for abdominal washing of abdomen and closure of the fascia. Postoperatively the patient developed an enterocutaneous fistula which was managed by TPN and abdominal wound vac. Patient was discharged to home two months after the initial procedure. 3 months after the initial procedure a postoperative CT scan of the abdomen and pelvis revealed no evidence of tumor in the abdomen. Patient and family decided hospice care two months later.

Treatment of the Resected Surgical Margins

In the course of surgery, CAP treatment of the surgical margins (diaphragm, abdominal wall, mesentery, left colic gutter, mesenteric area, area of the splenic bed) was performed using the Canady Helios Cold Plasma™, Images of treatment of surgical margins by CAP showed partial resection of the diaphragm using the Canady Hybrid Plasma™ scalpel and cold plasma jet treatment of surgical margins after resection.

In addition to treatment of surgical margins we performed cold plasma treatment of the ex vivo sample of liver and diaphragm. Treated and untreated samples were imaged and analyzed using various assays.

Body Temperature Measurements

A thermal camera (FLIR A35) with a 19 mm lens and a 60 Hz framerate was used to collect the plasma object and patient body's thermal data. The FLIR A35 camera was mounted approximately 3 ft above the patient to observe the treatment area. To get a better viewing angle and to ensure that the camera is less intrusive to the surgeon's procedure, a less than 20° view angle was applied to the camera. The FLIR A35 thermal camera's area of view at approximately 3 ft is 2.7 ft by 2 ft area, which is larger than the 1 foot by 1 foot of the patient's procedure area. In total, 5 hours of thermal video was captured by the camera and stored onto the hard drive of the control PC. During the procedure, the patient was treated with the Canady Hybrid Plasma™ and the Canady Helios Cold Plasma™ scalpels. The treatments consisted of "spraying" the margins of the cancerous area with the cold plasma jet created at the distal end of the Helios Cold Plasma Scalpel. The settings for the Canady Helios Cold Plasma™ Ablator's settings were 1.6 W and helium flow rate 5 L/min for a duration of 2 min per treatment area.

Figure 10:
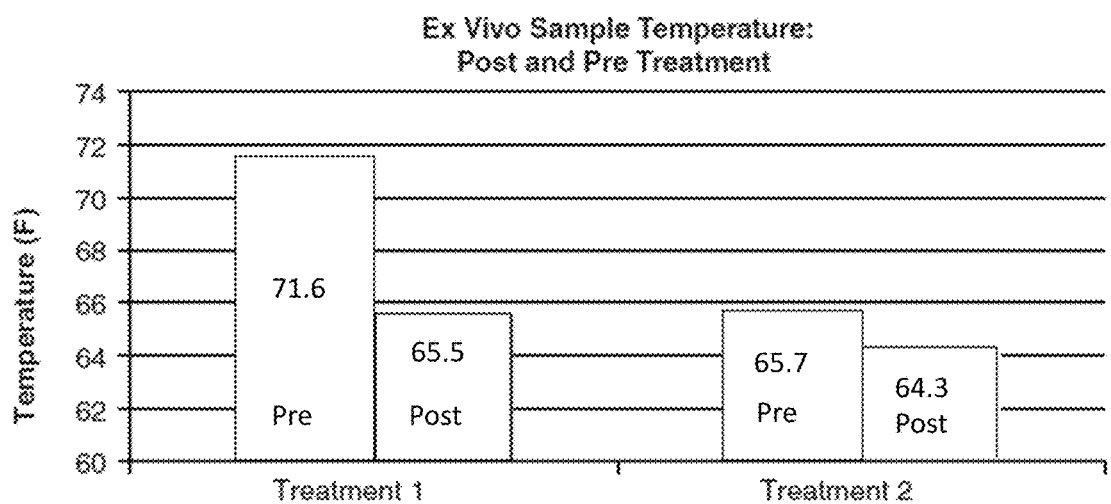
FIG. 10 is a graph of Ex vivo cold plasma treatment results, showing the temperature measured before and after the treatments. There is a slight temperature decrease between pre-treatment and intraoperative treatment, but not as large as in the case of the patient.

The data captured by the FLIR camera was later processed using FLIR tools+. See, Lahiri BB, Bagavathiappan S, Jayakumar T, Philip J. Medical applications of infrared thermography: a review. Infrared Phys Technol. 2012; 55(4): 221-35. To compare the cold plasma intraoperative thermal performance and patient's tissue reaction to the cold plasma scalpel, the patient's pre-treatment area tissue temperature and post-treatment tissue area temperature were measured. Tissue area temperature was calculated by taking the average of the temperature data in the treatment area by using the built-in functions of FLIR tools+, FIG. 10 illustrates a side by side comparison of tissue temperature pre-treatment and post-treatment.

Along with intraoperative cold plasma treatments, the thermal camera recorded several cold plasma ex vivo treatments. The tumor cells and a small amount of normal cells were removed from the patient for a comparison study; tumor and control samples were treated with the cold plasma scalpel with the same settings as the intraoperative treatments. The pre-treatment and post-treatment thermal images for ex vivo were processed identically to the intraoperative treatments. During the data processing, FLIR tools+built in functions were selected to measure the treatment area's minimum, maximum, and average temperatures. Based on the background reference material, a thermal emissivity of 0.95 was selected, so as to best represent the actual temperature of live body tissues for the spectral range of the camera (7.5-13 μm). During the procedure, the patients End Tidal CO2 and O2 level were recorded via the ventilator and the pulse oximeter respectively.

Figure 9:
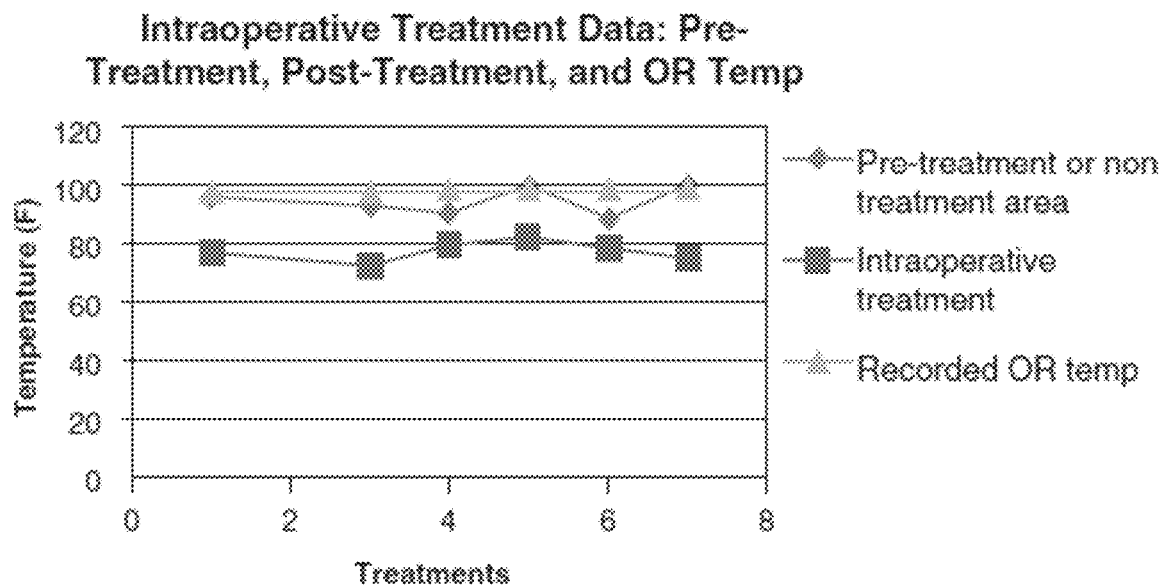
FIG. 9 is a graph of interoperative temperature showing the temperature before and after CAP treatment as well as the temperature measured by the OR equipment.

Thermal measurements from the in vivo treatments are shown in FIG. 9. Significant temperature change occurs in the area of treatment for each case. A temperature drop of 10-20° across the surface of the tissue occurs in all six treatments. Temperature measurements of the surrounding tissue and tissues pre-treatment are displayed as well and are consistent with the core temperature measured with the hospital's equipment.

Figure 11:
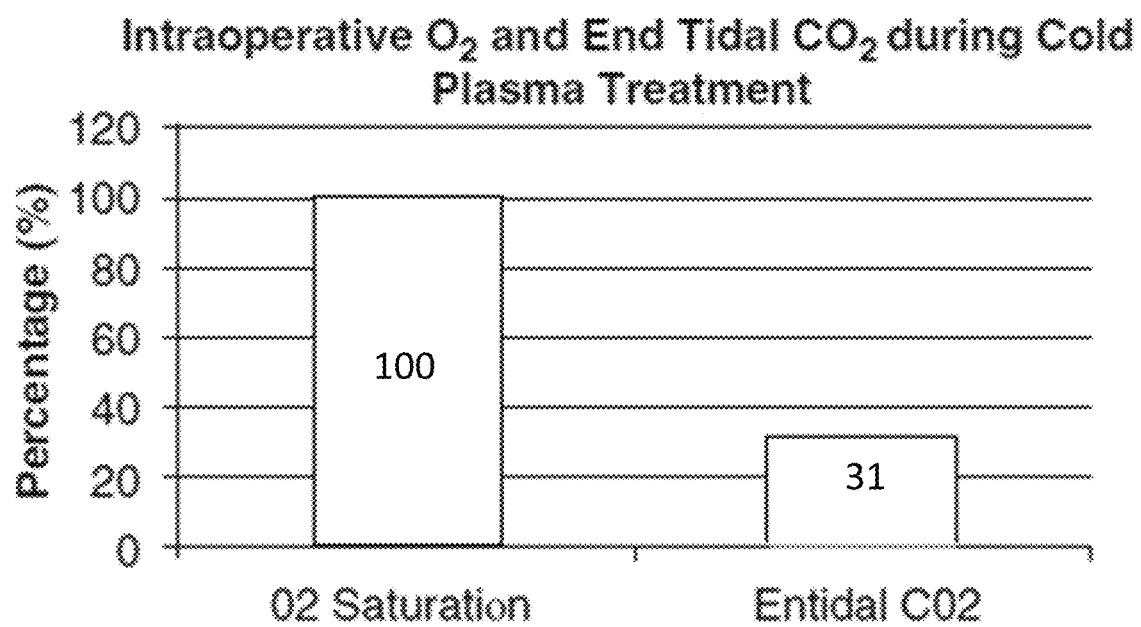
FIG. 11 is a graph of O2 and End Tidal CO2 results for the patient during the treatments. The patient intraoperative O2 and End Tidal CO2 measurements were unaffected by the treatment and were well within the normal range throughout the treatments as shown in FIG. 10.

Expansion In Vitro, Characterization and Immunohistological Analysis of Human Primary Colon Cancer Epithelial Cells Isolated After Surgery In this Section we describe characterization of the human primary colon cancer cells. Identification of colon stem cell markers CD44 and TRAIL receptor 1 were performed (FIGS. 10 and 11).

Human Tissue Preparation and Sample Collection

Human tissue was handled according to the tenets of the Declaration of Helsinki. On the basis of our studies in vitro using primary LT-97-3 colon cancer stem cells (Generous gift of Dr. Brigitte Marian, Univ. of Vienna Medical Center, Austria; J Pathol. 2007 October; 213(2):152-60), HCT-116 ATCC derived Colon cancer cells and normal colon epithelial cells (unpublished data) we chose to use the LT-97-3 medium for developing primary cultures. Medium used to culture the human LT-97 includes the following components, 4 parts Ham F12, 1 part L15, 2% FCS, insulin, 20 nm Triiodotyronin, Trasnferrin-20 μL for 500 mL, 1 μg/mL hydrocortisone-20 μL, 30 ng/mL EGF-15 μL, Penicillin 10,000 μg/mL (5 mL) /Streptomycin (5 mL)/gentamycin (2.5 mL) (Sigma Aldrich). The samples were collected in 20 mL sample collection vials containing the above medium at 4° C. and brought back to the lab within 10 h from the sample collection site and processed immediately.

31 Colon tumor explants was minced to 1 mm size and was processed to isolate epithelial cells using enzymatic digestion with 1 mg/mL collagenase type IV for 10 min at 37° C. and some of the 1 mm samples were expanded in vitro as explant cultures. The human colon epithelial cultures were expanded in a BSL2 classified laboratory (Jerome Canady Research Institute for Advanced Biological and Technological Sciences, Takoma Park, Md.) for maintaining cell lines for biomedical, translational and regenerative biology applications. Five freshly isolated human colon cancer samples were procured within 10 h of patient's surgery in sterile 20 mL borosilicate sample collection vials containing the above-mentioned medium composition.

3-5 cm2 or larger size of the colon tumor and normal tissue samples excised from the patient were used in the current study: (1) liver tissue with colon cancer treated with CAP (2) liver tissue with colon cancer treated without CAP (3) Subphrenic Diaphragm with colon cancer treated with CAP (4) Subphrenic Diaphragm with colon cancer treated without CAP and (5) normal diaphragm with and without CAP. Tissues were treated with penicillin streptomycin in PBS and minced and processed as described previously Ray S, et al. Establishment of human ultra-low passage colorectal cancer cell lines using spheroids from fresh surgical specimens suitable for in vitro and in vivo studies. J Cancer. 2012; 3:196-206. Normal diaphragm tissues were processed for cryosectioning and H&E staining. These two methods of cell culture namely, explant cultures and isolated cells cultures were used in the current study to generate primary using the patient's biopsy samples. Only two explants developed into epithelial cultures from tissues isolated with enzymatic treatments. The cells were serially diluted (into six 35 mm well plates) with the hope that the stem cells would develop and proliferate into colonies. All cultures were terminated for the following tests for histology, confocal microscopy to detect various proteins/antigens. Images were acquired periodically to assess the morphology of the cells.

Immunofluorescence Analysis for Identification of Colon Stem Cells and Colon Cancer Markers in Tissues Excised Using Cold Plasma Scalpel Some of the tissues procured from the patient were immediately cryosectioned using Leica cryostat. 5-6 µm sections at −20° C. were stained with H&E and double immunofluorescence for localization of colon stem cell marker human CD44 FITC (Bio Legend), anti-TRAIL receptorl (Santa Cruz) and second antibody anti-alexaflour 594 or 488 (molecular probes), respectively was used along with nuclear counterstaining with DAPI (Vectashield, Molecular Probes). Appropriate isotype controls (Life Technologies) were maintained. Zeiss confocal images were acquired to analyze the cold plasma excised tissue for remnant colon cancer markers.

Confocal Imaging

Zeiss 1 um tick Z-stack images were acquired and 3D-reconstruction of the images (Jerome Canady Research Institute for Advanced Biological and Technological Sciences, Takoma, Park, Md.) were analyzed for surface expression of TRAIL-R1 and CD44 or Ki67 in the cryosections (n =3) and in cultured colon cancer cells after 30 days in culture. The entire dish was assessed, and images were captured for the remnant cells and the % of positive cells was calculated. 15 images per dish were acquired to record the % total number of cells remaining and % of cells positive for the above markers.

Statistical Analysis

The following test was carried out for n=3 samples. Nonparametric Tests: Independent Samples. NP tests/independent Test-Mann Whitney Wald Wolfowitz Kruskal Wallis test compared pair wise; median(test value=sample=compare=pairwise) Hodges Lehmann/missing Scope=analysis usermissing=exclude/criteria with alpha=0.05 Cilevel=95.

Results

Metastatic Liver With and Without CAP Treatments

FIGS. 12A and 12B shows cross sections images along the thickness of the sample excised from the patient. Note the intactness of the tissue sections in 10A and 10B showing no damage at the site of CAP treatments (arrow). Arrowhead indicates the metastatic colon cancer area in the liver. These tissues were used to isolate the colon cancer cells to be cultured and expanded in vitro for further analysis.

Metastatic Tumor from Sub Phrenic Diaphragm with and without CAP Treatments

Figure 13A:
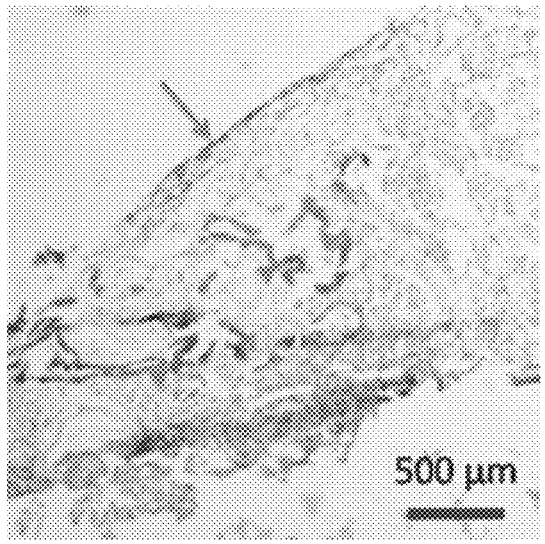
FIGS. 13A and 13B are images of H&E stained sections showing Metastatic Tumor Sub phrenic Diaphragm (FIG. 13A) treated with cold plasma and (FIG. 13B) without Cold Plasma treatment.
Figure 13B:
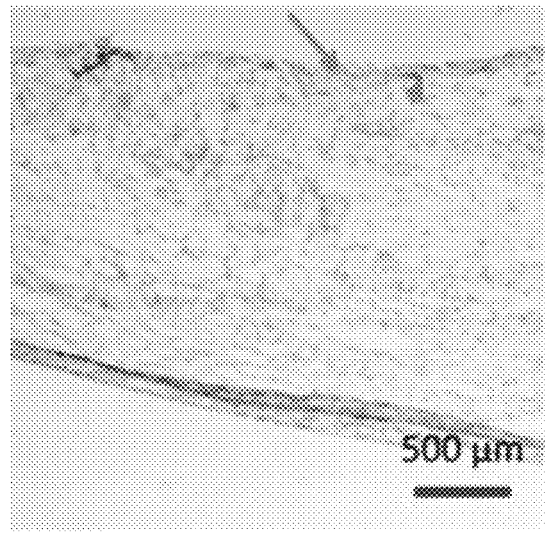

FIGS. 13A and 13B show images, which are cross sections along the entire thickness of the sample excised from the patient. Note the intactness of the tissue sections in a and b showing no damage at the site of CAP treatments (arrow). Arrowhead indicates the metastatic colon cancer area in the sub phrenic diaphragm. These tissues were used to isolate the colon cancer cells to be cultured and expanded in vitro for further analysis.

Figure 14A:
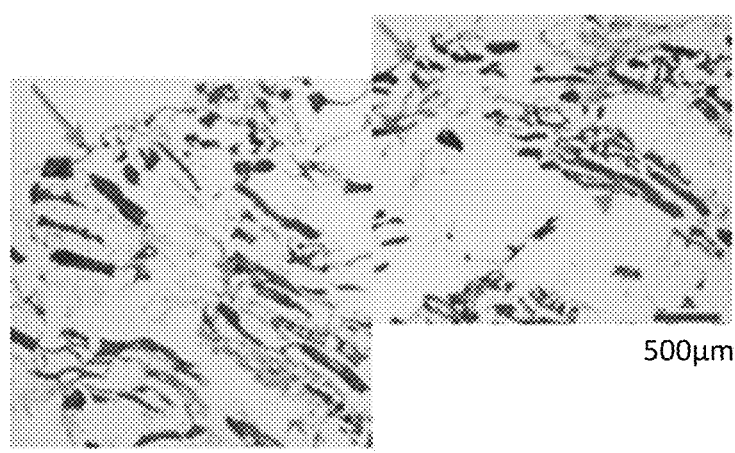
FIGS. 14A and 14B are images of H&E stained sections showing (FIG. 12A) Normal Diaphragm treated with CAP treatment and (FIG. 12B) without CAP treatment.
Figure 14B:
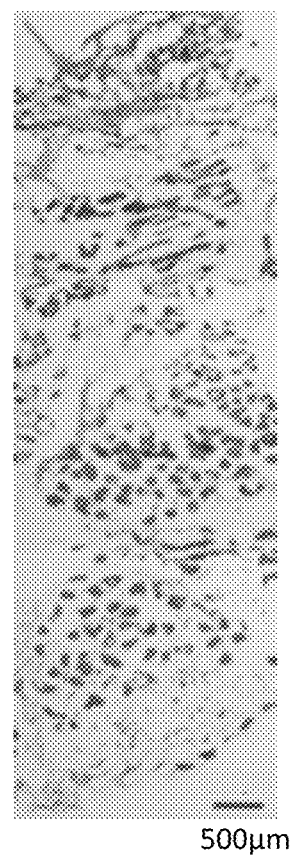

Normal Diaphragm With and Without CAP Treatments, to Demonstrate That CAP Does Not Cause Injury to the Healthy Tissues Images in FIGS. 14A and 14B are cross sections along the thickness of the sample excised from the patient. Note the intactness of the tissue sections in a and b showing no damage at the site of CAP treatments (arrow). Arrowhead shows muscle fibers of the diaphragm separated by loose connective tissue.

Confocal Double-Immunofluorescence Images of Human Liver Showing Localization of Colon Stem Cells (CD44 Positive Red) and TRAIL-Receptor 1 (Green)

Figure 15A:
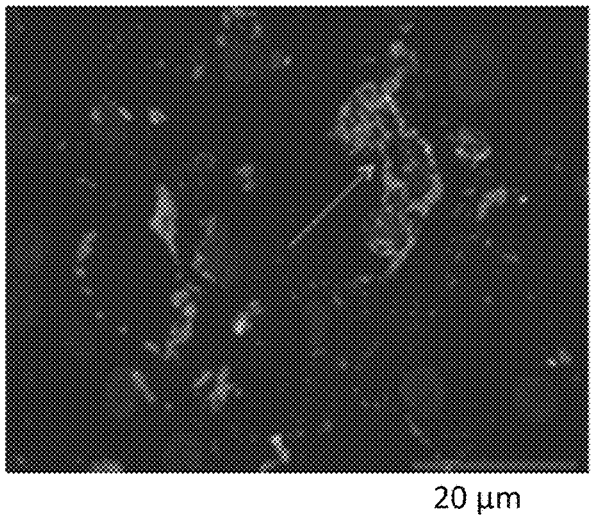
FIGS. 15A-15D are Confocal Immunofluorescence images of human Liver demonstrate localization of colon stem cells (CD44 positive red) and TRAIL-Receptor 1 (green) (arrow-a to d). DAPI was used for nuclear counterstaining.
Figure 15B:
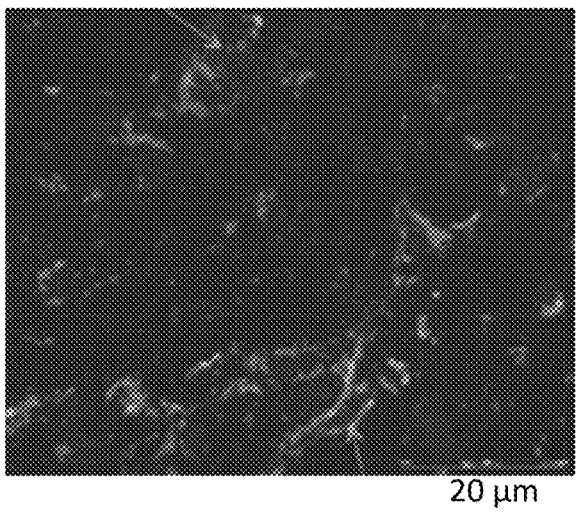
Figure 15C:
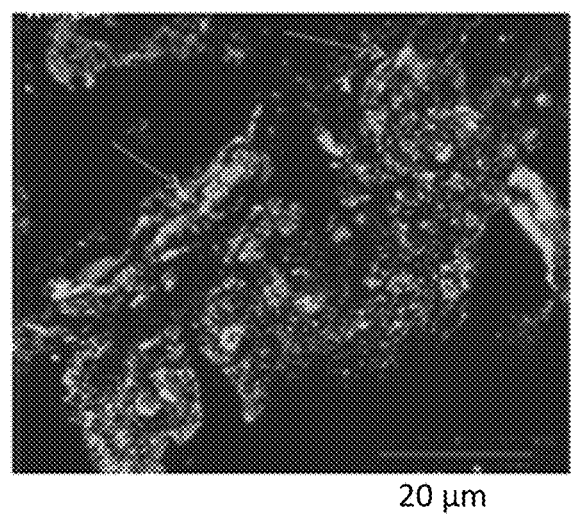
Figure 15D:
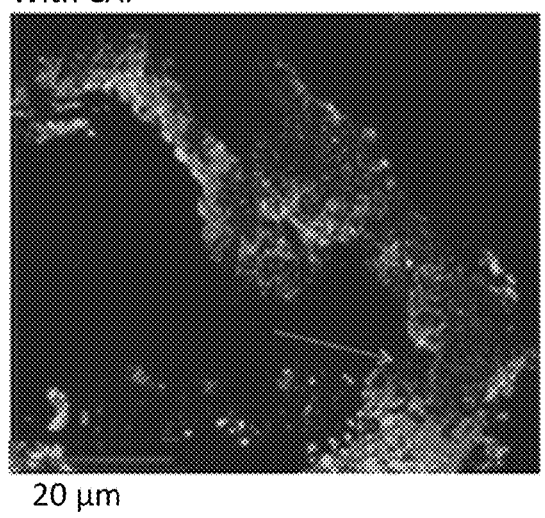
Figure 16A:
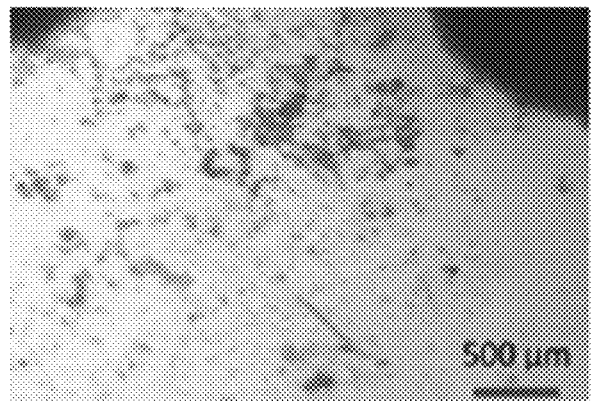
FIGS. 16A-16D are images showing in vitro expansion of Human colon Cancer cells from liver samples treated with CAP. Representative images of explant (a) and isolated cell cultures (b-d) of colon cells from liver showing cell death and many floating dead cells (arrow) and differentiated cells (arrowhead) in the presence of CAP after 17-27 days in culture (b-d). Note the absence of outgrowth in the liver explant cultures.
Figure 16B:
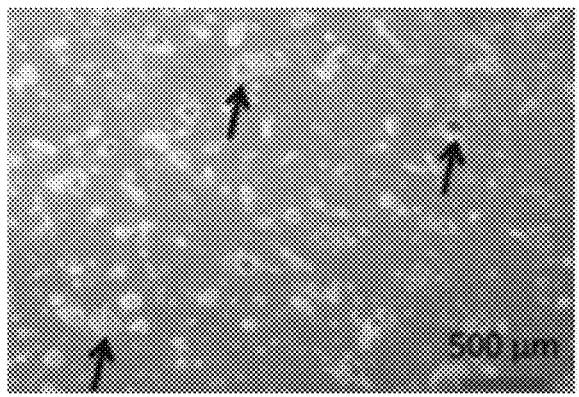
Figure 16C:
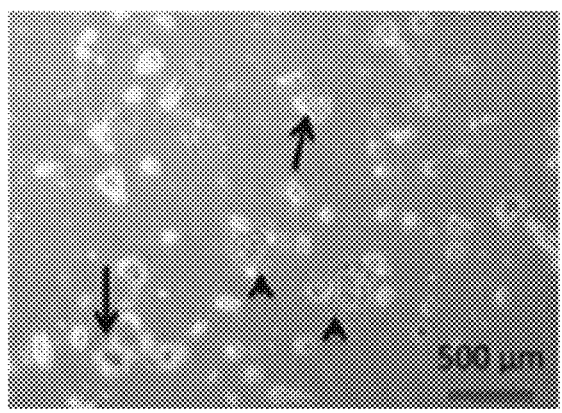
Figure 16D:
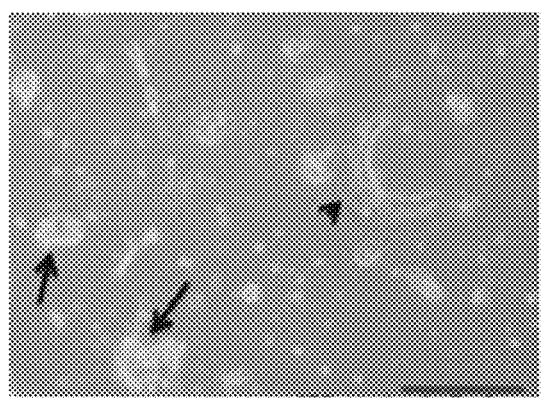
Figure 17A:
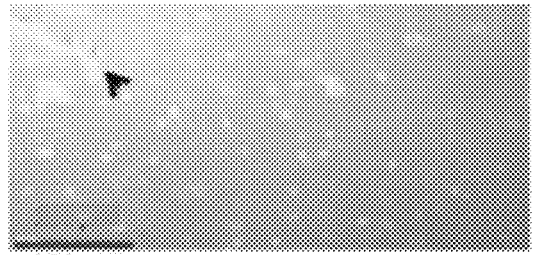
FIGS. 17A-17D are representative images of isolated cell cultures of colon cells from liver showing healthy proliferating colony of cells (arrowhead) without CAP after 17 (a) to 24 days (b-d) in culture.
Figure 17B:
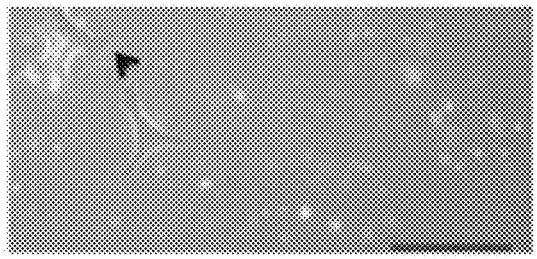
Figure 17C:
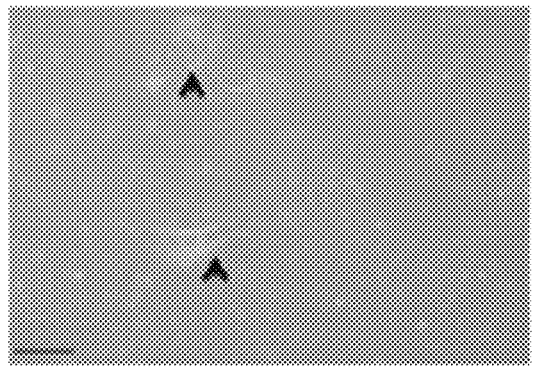
Figure 17D:
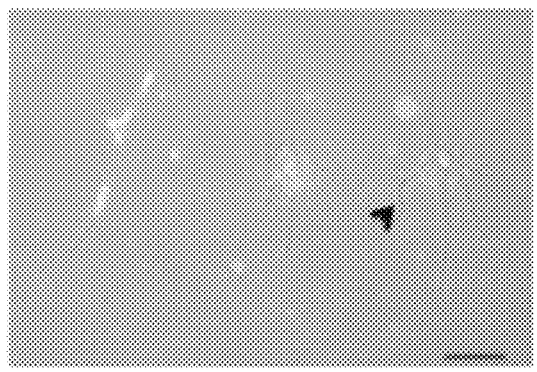
Figure 19A:
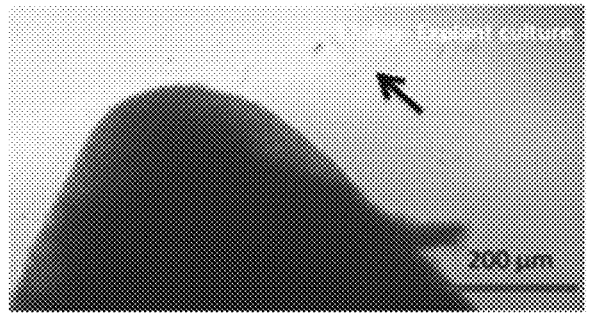
FIGS. 19A-19F are images showing in vitro expansion of Human Colon Cancer cells from Sub phrenic Diaphragm samples without CAP treatment. Cellular profile of the sub phrenic diaphragm showing proliferating colony of cells (arrow) without CAP after 17-27 days in culture (b, d, f). Note the large colony, a property of a tumor stem cell. Explant cultures show fibroblast-like phenotype.
Figure 19B:
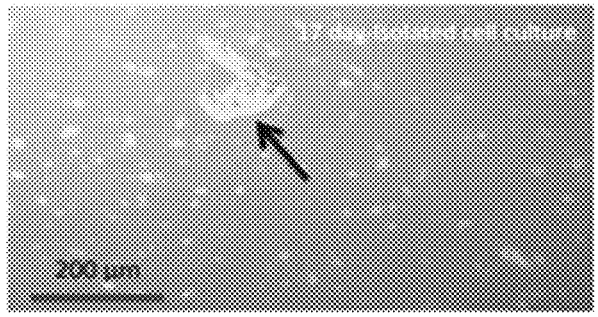
Figure 19C:
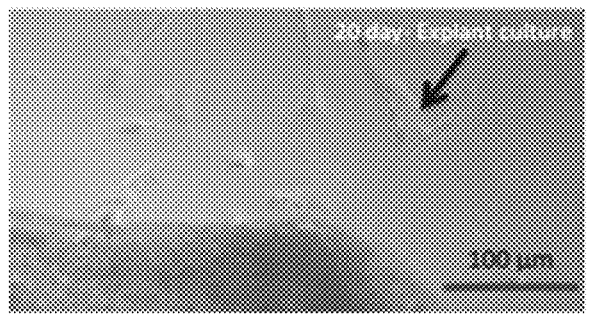
Figure 19D:
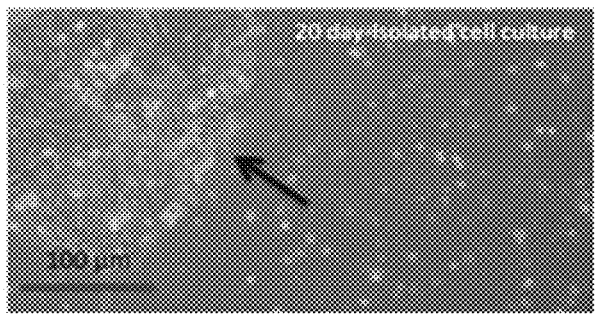
Figure 19E:
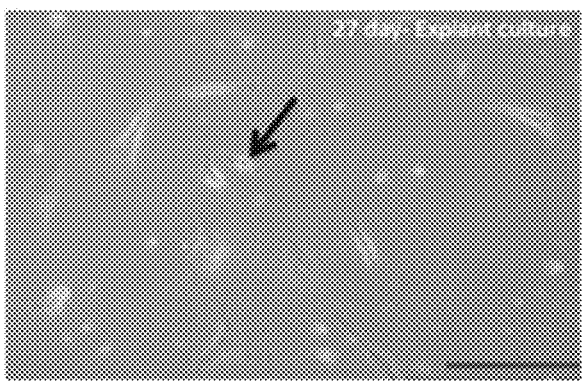
Figure 19F:
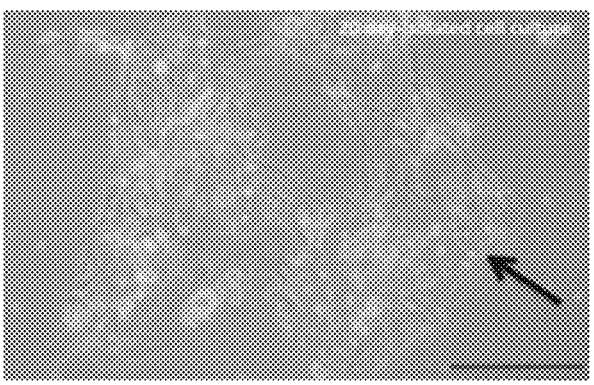
Figure 20A:
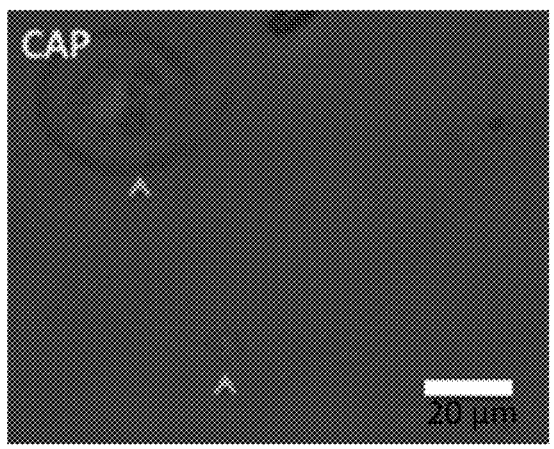
FIGS. 20A-20D are images showing characterization of colon cancer cells expanded in vitro isolated from liver nuclear counterstaining with DAPI (blue).
Figure 20B:
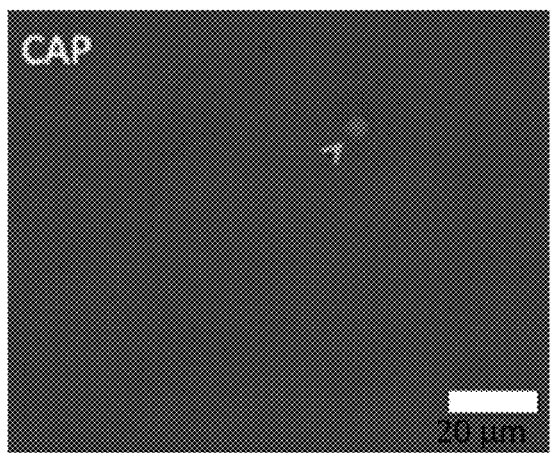
Figure 20C:
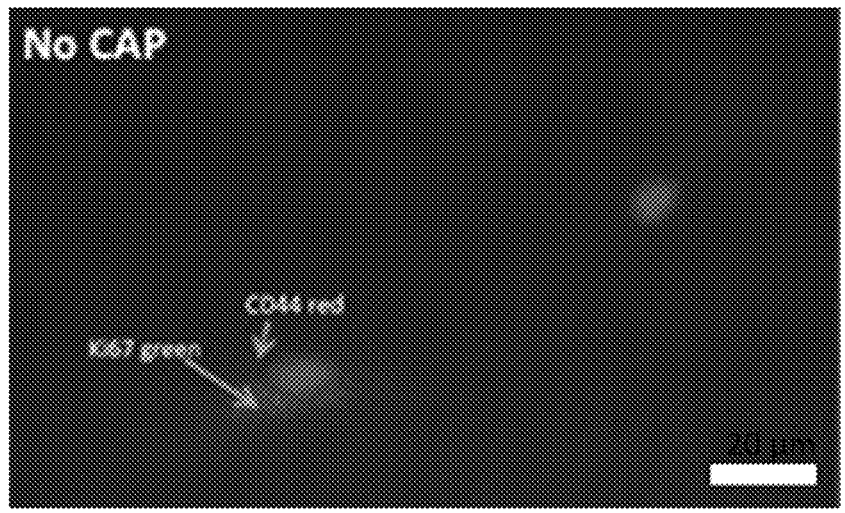
Figure 20D:
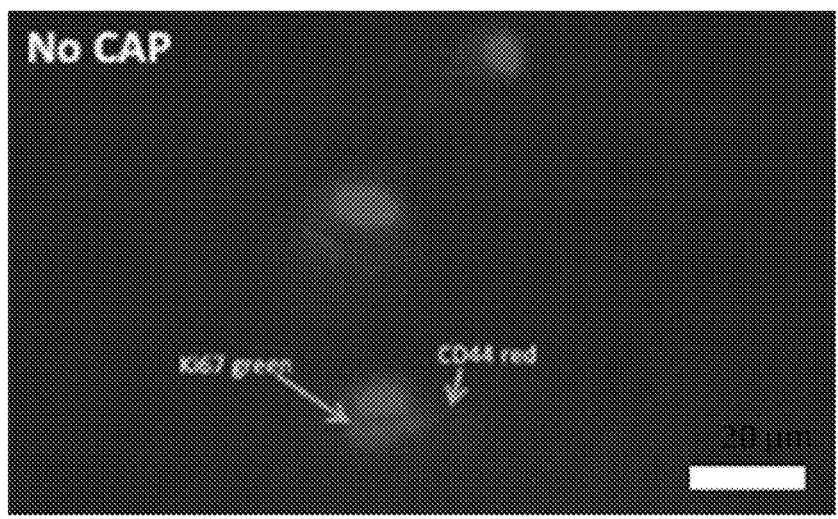

FIGS. 15A and 15B are samples without CAP treatments and FIGS. 15C and 15D are with CAP treatments. Note the bright TRAIL R-1 staining in FIGS. 15C and 15D in presence of CAP and the absence of bright TRAIL-R1 in FIGS. 15A and 15B.

Freshly procured human tumor samples from liver treated with and without CAP were oriented and embedded in the cryostat. 6-7 µm thick sections and fixed in ice-cold methanol for 15 min and double-immunostained for TRAIL-R1 and CD44. In the presence of CAP treatments, the TRAIL-R1 expression increases. Moreover, the double positive cells expressing CD44 and TRAIL-R1, typical of a stem cell was observed in all the tumor samples as shown in FIGS. 15A-15D. It was found that the localization and expression of TRAIL-R1 in the CAP treated CD44 positive cell was greater in both number and expression (FIGS. 15C-15D). These results suggest that CAP triggering of TRAIL-R1 in colon cancer stem cells may play a role in apoptosis. Therefore, we isolated and expanded the cells from these CAP treated and untreated tumor samples to further characterize the cellular profile.

In Vitro Expansion of Human Colon Cancer Cells from Liver Samples Treated with CAP In order to test for characterization of cellular profile generated from tissue explants with and without CAP, two different in vitro culture methods were employed (materials and methods). It was interesting to note that explant cultures of liver did not show any outgrowth of cells, while cells isolated using enzymatic treatments, yield a varied population of cells. FIGS. 16A-16D demonstrate that the CAP treated tissue yielded a population of epithelial cells, which over a period of time showed morphology of mostly differentiated cells in the terminal phase of apoptosis. Most of the cells were floating in culture demonstrating an apoptotic phenotype.

In Vitro Expansion of Human Colon Cancer Cells from Liver Samples without CAP Treatment The explant cultures showed no outgrowth, while the cells isolated from liver samples showed small colonies and proliferating colonies as shown in FIGS. 17A-17D (arrowhead a, b). This colony was tracked, and the colony size increased over time (a, b). After more than 3-weeks of culture these cells were still proliferating (arrowhead). These cultures were terminated to assess the molecular characteristics using various markers.

In Vitro Expansion of Human Colon Cancer Cells from Subphrenic Diaphragm Samples Treated with CAP The cellular profile and phenotype from CAP treated sub phrenic diaphragm (FIGS. 18A-18F) showed epithelial cells going through apoptosis. However, the explant cultures showed fibroblast-like cells, which may not be of colon cancer origin and may be from the remnant diaphragm tissue. The isolated cell cultures showed floating dead cells at the end of 27th day.

In Vitro Expansion of Human Colon Cancer Cells from Sub Phrenic Diaphragm Samples Without CAP Treatment Sub phrenic diaphragm without CAP treatment (FIGS. 19A-19F) showed colon epithelial stem cell phenotype. The small colony enlarged over a period of time showing colon stem cell phenotype (b, d, f). However, the explant cultures showed fibroblast-like cells, which may not be of colon cancer origin and may be from the remnant diaphragm tissue.

Characterization of Colon Cancer Cells Expanded In Vitro Isolated from Liver Isolated cell cultures of colon cells from liver showing disintegrating nuclei of smaller size in (arrowhead in a, b) Note these cells are negative for Ki67 and TRAIL-r1, suggesting that these cells are in last phase of apoptosis. (b) Showing healthy proliferating colony of cells (arrow; green Ki67 positive and red-TRAIL-R1 positive) without CAP after 30 days in culture.

Most of the cells display disintegrated nuclei and a few differentiated large cells in the presence of CAP treatment as shown in FIGS. 20A-20D. The smaller size of the nuclei and absence of any cytoplasmic material was suggestive of a dead cell phenotype after CAP treatment. Large number of proliferating Ki67 positive cells were observed in cultures without CAP treatment and such cells were more in number when compared to the CAP treated. These results suggested that the profile of cells after CAP treatment was significantly different from the healthy proliferating tumor cells, generated from samples without CAP treatment. Therefore, in order to further characterize these cells for their proliferation we measured Ki67 along with TRAIL-R1 and the % total of positive and double positive cells in CAP treated and untreated cells was calculated.

Characterization of Cellular Profile of Human Colon Cancer Cells Expanded In Vitro Our analysis suggests that all the cells went through cell death and apoptosis in the CAP treated case. Recall that this proliferative population of cells was absent in the CAP untreated samples. About 40% cells were proliferating (Ki67 positive) and 24% cells expressed TRAIL-R1 in CAP untreated, while CAP treatment lead to cell death and apoptosis as shown in Table 9.1. None of the CAP treated cells expressed TRAIL-R1 and were not proliferating, suggesting that these cells were no longer viable, and their apoptotic mechanism was initiated by CAP treatment. These results suggest that CAP has an effect in inducing colon stem cell death by triggering TRAIL Receptor-1 expression.

Example 1 Conclusions

The above examples of the use of cold atmospheric plasma in a clinical setting for the treatment of metastatic stage IV colon cancer and demonstrate the safety and efficacy of cold atmospheric plasma. The human colon cancer in the patient samples expressed colon stem cells in liver and was positive for CD44 and TRAIL-R1 expression. TRAIl-R1 expression increases in the CAP treated liver tissues, suggesting that the death receptor molecule may be involved in inducing apoptosis. Isolation of colon epithelial cells from these livers and subphrenic diaphragm explants after CAP treatment, induced cell death within 3 weeks of culture. CAP untreated tissues yield a population of cells that are healthy and colonies increase in size, typical of tumor stem cells. These colonies proliferated even after 4 weeks in culture. In addition, explant cultures after treatments with CAP and without treatments yielded fibroblast-like cell phenotype only in the subphrenic diaphragm samples and not from liver explants. These results suggest that these may be normal healthy cells and not the colon cancer epithelial cells and may require further investigation. It has to be noted that none of the CAP treated cells after 3-weeks of culture expressed TRAIL-R1. Moreover, the nuclei of remnant cells were all disintegrated and were significantly different from the population of CAP untreated proliferating Ki67 positive cells. FIG. 21 is a table illustrating characterization of cellular profile of human colon cancer cells expanded in vitro. The entire culture dish was analyzed to calculate proportion of total number of cells. Significant (*$p<0.05$) difference in the profile was cells with CAP treatment and without treatment was observed. Note the absence of TRAIL-R1 and Ki67 positivity in CAP treated samples.

Overall, the results suggest that CAP has an effect on colon epithelial cells and colon stem cells and induces tumor cell death and the use of CAP had no adverse event to the patient.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for treating cancer comprising:
pre-operatively providing at least one of radiation and chemotherapy to a patient having a cancerous solid tumor;
performing intra-operative resection of at least a portion of said solid tumor;
applying cold atmospheric plasma intra-operatively to margins surrounding an area from which the solid tumor was resected; and
post-operatively performing at least one of radiation and chemotherapy to the patient.

2. The method for treating cancer according to claim 1, further comprising:
intra-operatively performing hyperthermic intraoperative peritoneal chemotherapy on said patient.

3. The method for treating cancer according to claim 1, wherein said step of applying cold atmospheric plasma intra-operatively to margins surrounding the area from which the solid tumor was resected comprises:
selecting through a graphical user interface on a computing device a particular soft tissue sarcoma cell line associated with said solid tumor;
retrieving, with said computing device, cold atmospheric plasma settings data from a database of cancer cell line data and associated cold atmospheric plasma settings data in a storage; and
applying, with said computing device, said retrieved settings data to a cold atmospheric plasma system; and
treating said margins with cold atmospheric plasma supplied by said cold atmospheric plasma system using said retrieved cold atmospheric plasma settings data.

4. A method for treating cancer according to claim 3, wherein said cold atmospheric plasma settings data in said database are based upon a predicted cold atmospheric plasma effectiveness derived from testing a plurality of soft tissue sarcoma cell lines with cold atmospheric plasma treatment at a plurality of settings.

* * * * *